(12) United States Patent
King

(10) Patent No.: US 7,689,289 B2
(45) Date of Patent: Mar. 30, 2010

(54) TECHNIQUE FOR ADJUSTING THE LOCUS OF EXCITATION OF ELECTRICALLY EXCITABLE TISSUE WITH PAIRED PULSES

(75) Inventor: Gary W. King, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 960 days.

(21) Appl. No.: 11/277,207

(22) Filed: Mar. 22, 2006

(65) Prior Publication Data

US 2007/0225765 A1 Sep. 27, 2007

(51) Int. Cl.
*A61N 1/18* (2006.01)
(52) U.S. Cl. .............................. 607/66; 607/70; 607/67
(58) Field of Classification Search .................. 607/2, 607/46, 66, 67, 70, 115, 116, 117, 148
See application file for complete search history.

(56) References Cited

U.S. PATENT DOCUMENTS

| | | | |
|---|---|---|---|
| 1,935,138 | A | 11/1933 | Windisch |
| 3,822,708 | A | 7/1974 | Zilber |
| 3,850,161 | A | 11/1974 | Liss |
| 3,918,461 | A | 11/1975 | Cooper |
| 3,920,024 | A | 11/1975 | Bowers |
| 3,957,036 | A | 5/1976 | Normann |
| 4,524,774 | A | 6/1985 | Hildebrandt |
| 4,543,955 | A | 10/1985 | Schroeppel |
| 4,548,203 | A | 10/1985 | Tacker, Jr. |
| 4,570,640 | A | 2/1986 | Barsa |
| 4,702,254 | A | 10/1987 | Zabara |
| 4,750,499 | A | 6/1988 | Hoffer |
| 4,867,164 | A | 9/1989 | Zabara |
| 4,877,032 | A | 10/1989 | Heinze |
| 4,964,411 | A | 10/1990 | Johnson |
| 5,002,053 | A | 3/1991 | Garcia-Rill |
| 5,018,523 | A | 5/1991 | Bach, Jr. |

(Continued)

FOREIGN PATENT DOCUMENTS

EP 0236513 9/1997

(Continued)

OTHER PUBLICATIONS

J. Holsheimer, Wilbert A. Wesselink, M.Sc., "Effect of Anode-Cathode Configuration on Paresthesia Coverage in Spinal Cord Stimulation," Institute for Biomedical Technology, Department of Electrical Engineering, Neurosurger, vol. 41, No. 3, pp. 654-660, Sep. 1997.

(Continued)

*Primary Examiner*—Carl H Layno
*Assistant Examiner*—Elizabeth K So
(74) *Attorney, Agent, or Firm*—Banner & Witcoff, Ltd.

(57) ABSTRACT

The locus of electrically excitable tissue where action potentials are induced can be controlled using the physiological principle of electrotonus. Substantially non-simultaneous first and second pulses are applied to first and second electrodes, respectively, to generate both first and second action potentials and first and second subthreshold potential areas, within the tissue. The locus within the tissue where additional action potentials are induced may be determined by a superposition of the first and second subthreshold areas according to the physiological principle of electrotonus. Superposition of the first and second subthreshold areas provides deep tissue suprathreshold potential areas of adjustable locus wherein additional action potentials are induced.

24 Claims, 18 Drawing Sheets

U.S. PATENT DOCUMENTS

| | | | |
|---|---|---|---|
| 5,025,807 A | 6/1991 | Zabara | |
| 5,081,990 A | 1/1992 | Deletis | |
| 5,121,754 A | 6/1992 | Mullet | |
| 5,167,229 A | 12/1992 | Peckham | |
| 5,314,458 A | 5/1994 | Najafi | |
| 5,314,495 A | 5/1994 | Kovacs | |
| 5,324,309 A | 6/1994 | Kallok | |
| 5,332,401 A | 7/1994 | Davey | |
| 5,370,665 A | 12/1994 | Hudrlik | |
| 5,501,703 A | 3/1996 | Holsheimer | |
| 5,507,788 A | 4/1996 | Lieber | |
| 5,713,922 A | 2/1998 | King | |
| 5,895,416 A | 4/1999 | Barreras, Sr. | |
| 5,925,070 A | 7/1999 | King | |
| 5,948,007 A * | 9/1999 | Starkebaum et al. | 607/67 |
| 6,038,480 A | 3/2000 | Hrklicka | |
| 6,083,252 A | 7/2000 | King | |
| 6,505,078 B1 * | 1/2003 | King et al. | 607/67 |

FOREIGN PATENT DOCUMENTS

| | | |
|---|---|---|
| WO | 9519804 | 7/1995 |

OTHER PUBLICATIONS

J. Holsheimer, J.J. Strujik, N.R. Ras, "Effects of Electrode Geometry and Combination on Nerve Fibre Selectrivity in Spinal Cord Stimulation," Institute for Biomedical Technology, Medical & Biological Engineering & Comput., vol. 33, pp. 676-682 (1995).

J. Holsheimer, G. Barolat, J.J. Strujik, J. He, "Significance of the Spinal Cord Position in Spinal Cord Stimulation," Institute for Biomedical Technology, Department of Neurological Surgery, Acta Neurochir (1995) [Suppl] 64: 119-124.

J. Holsheimer, J.J. Strujik, N.J.M. Rijkhoff, "Contact Combinations in Epidural Spinal Cord Stimulation," Stereotact Funct Neurosurg, vol. 56, pp. 220-233 (1991).

Kirsten E.I. Deurloo, Jan Holsheimer, "Transverse Tripolar Stimulation for Selective FNS," IEEE/EMBS Conference, Amsterdam (1996).

J.J. Strujik, J. Holsheimer, "Transverse Tripolar Spinal Cord Stimulation: Theoretical Performance of a Dual Channel System," Medical & Biological Engineering & Comput., vol. 34, pp. 273-279 (1996).

* cited by examiner

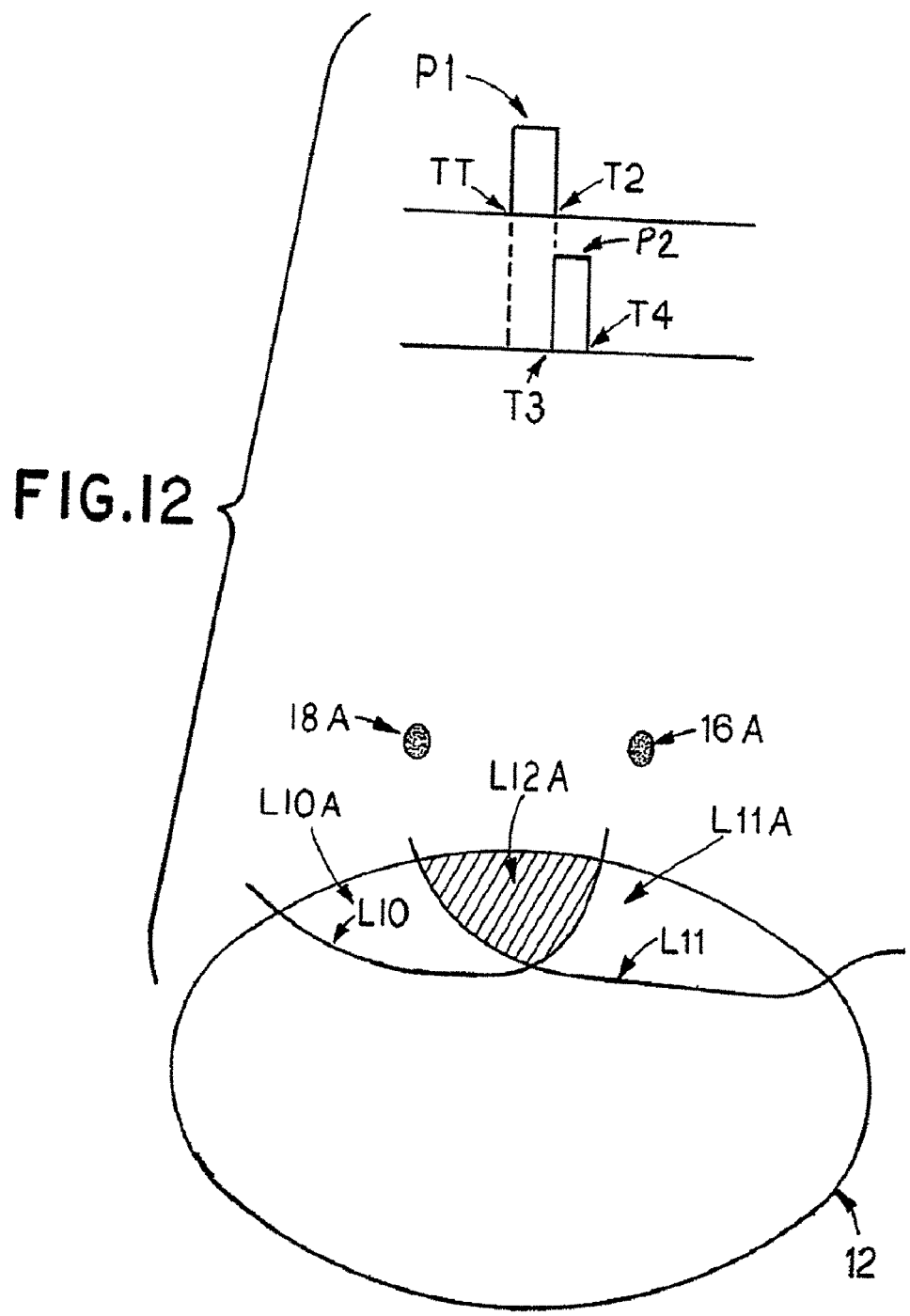

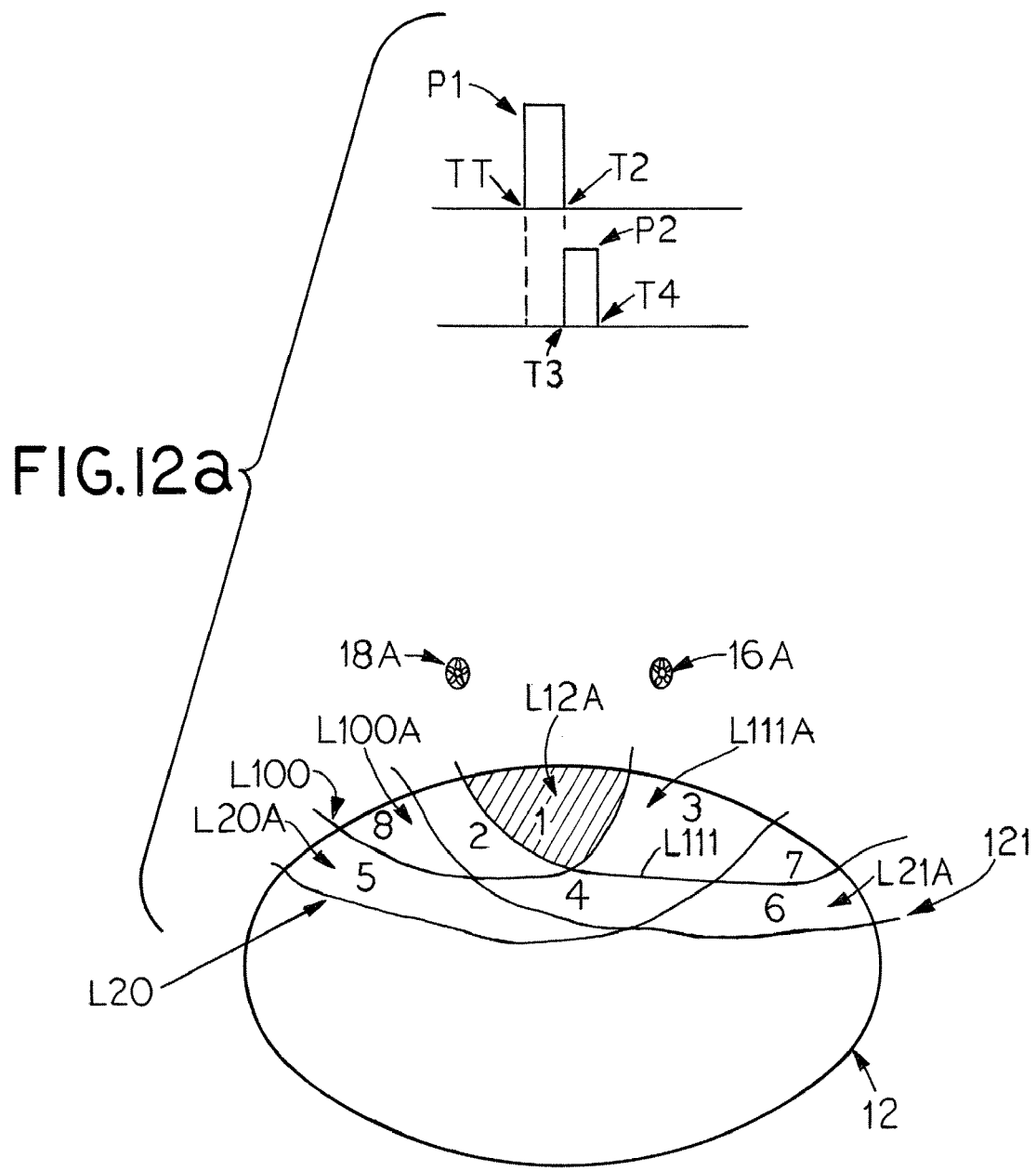

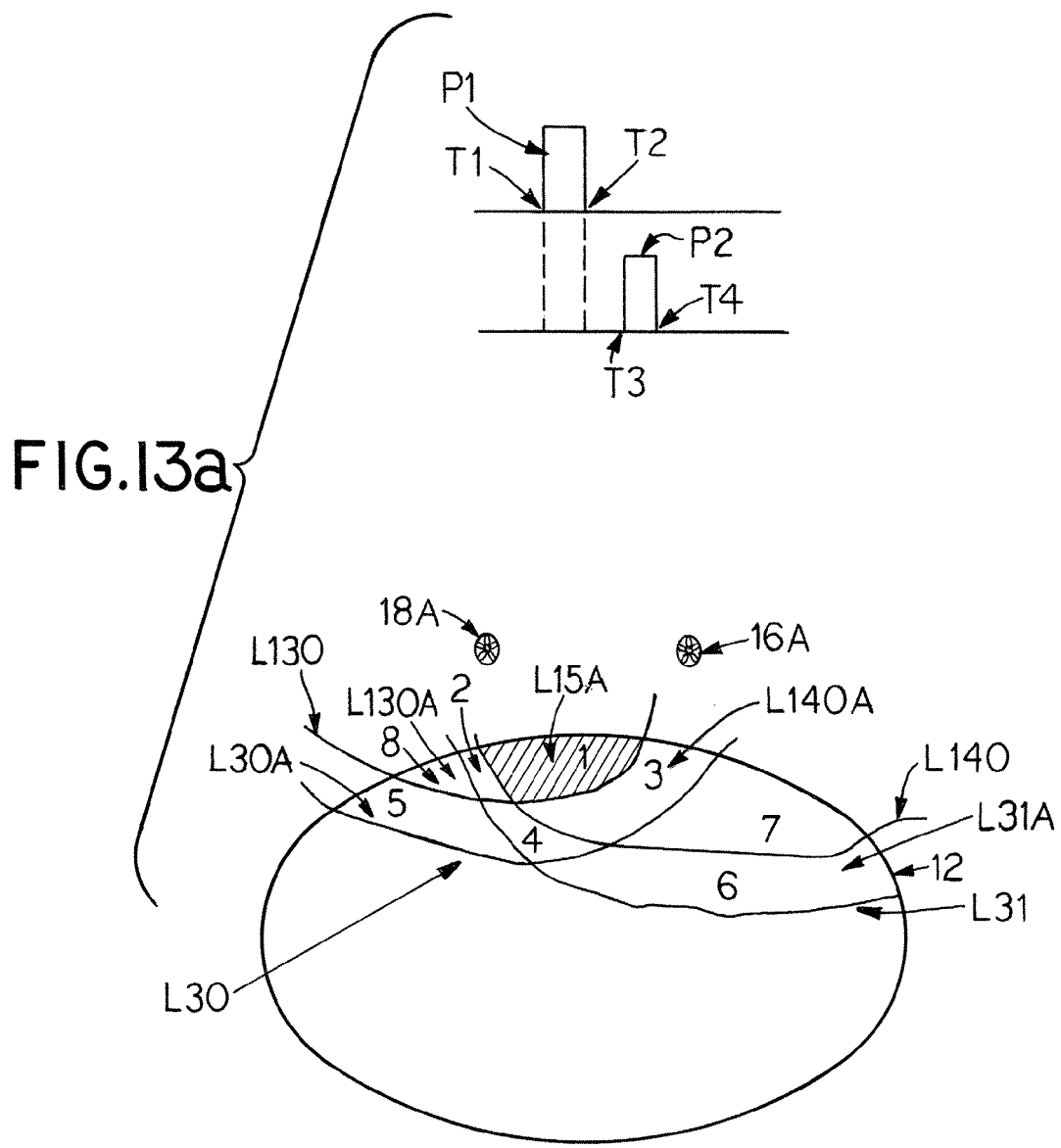

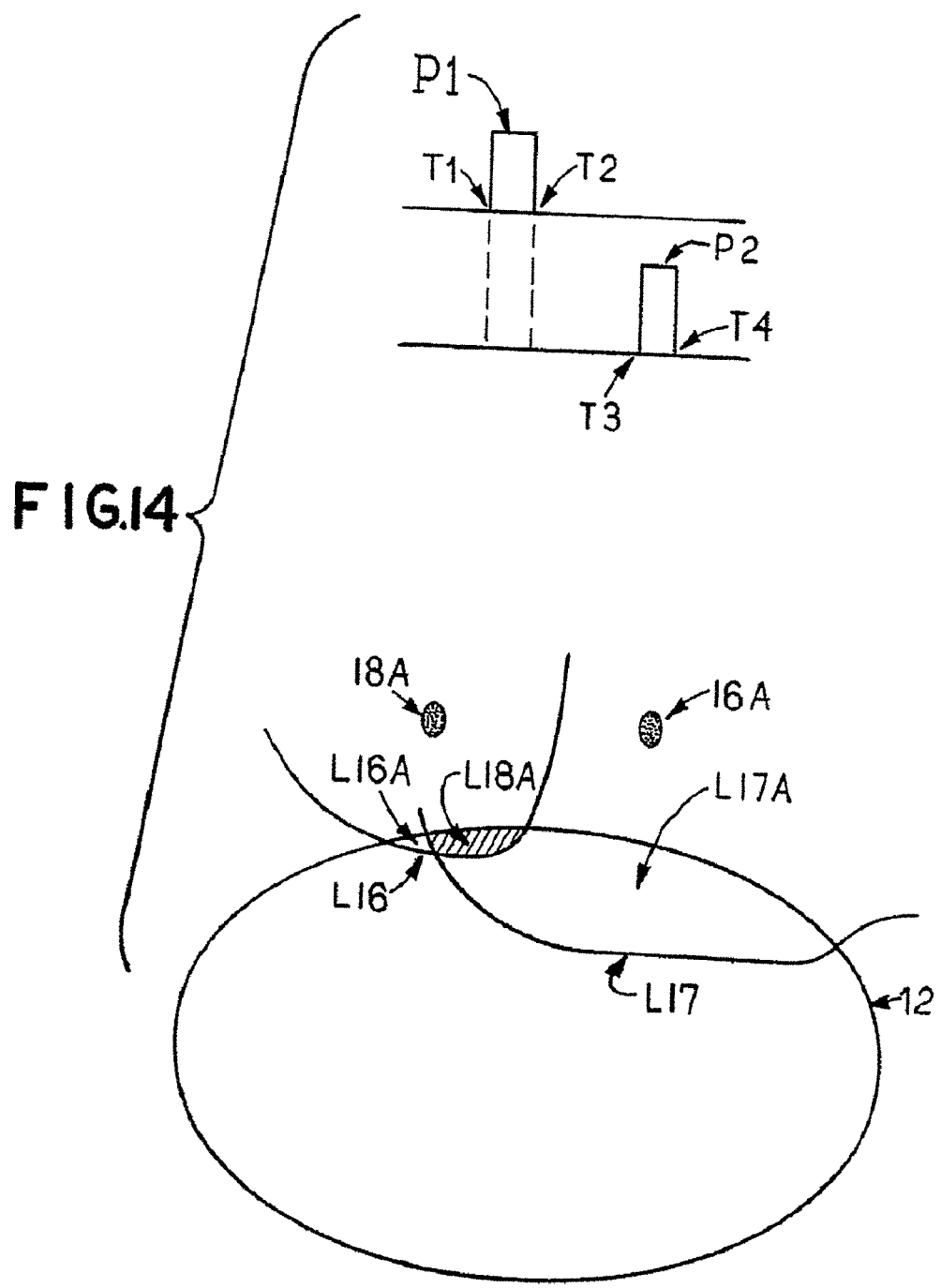

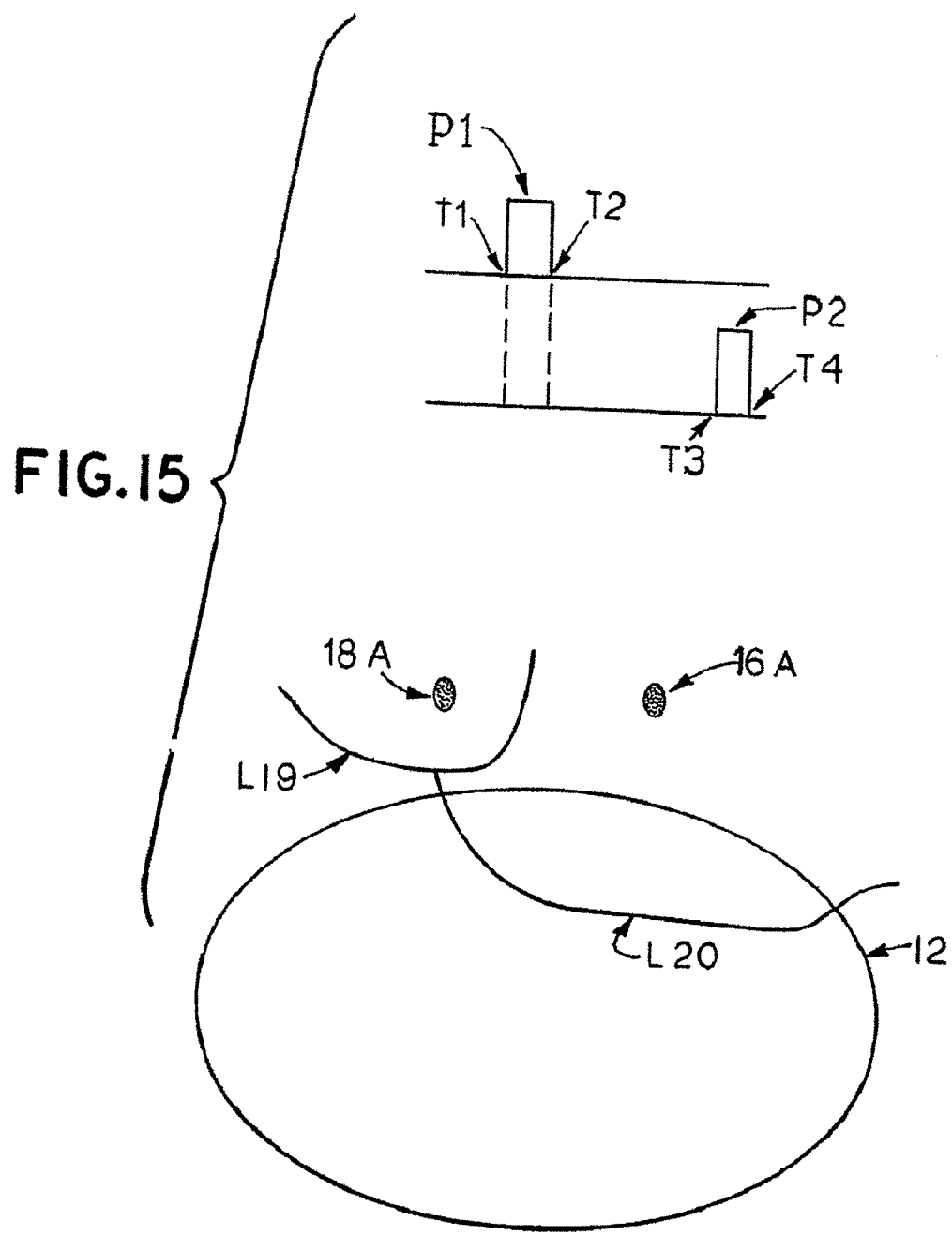

Figure 16
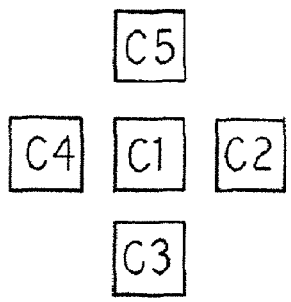
Figure 18
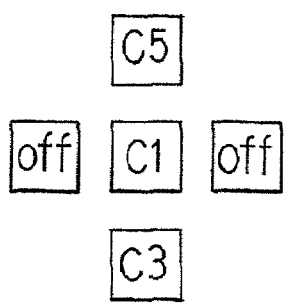
Figure 17
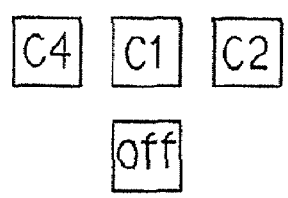
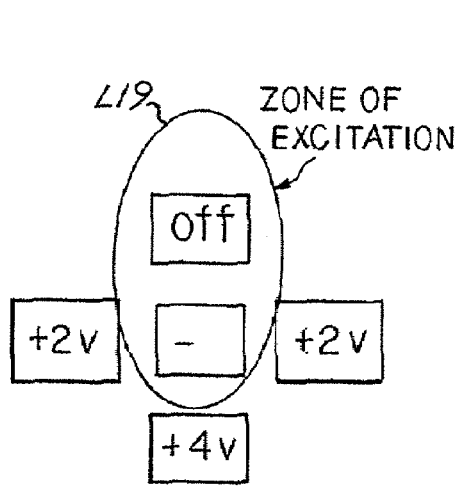
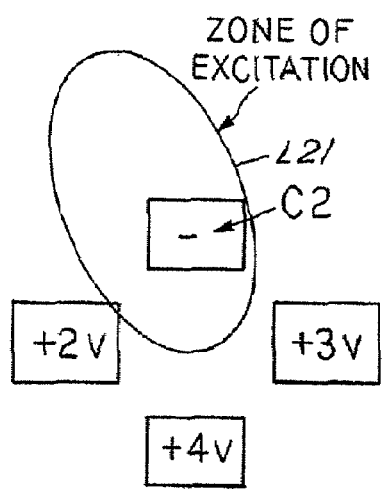
Figure 19    Figure 20    Figure 21
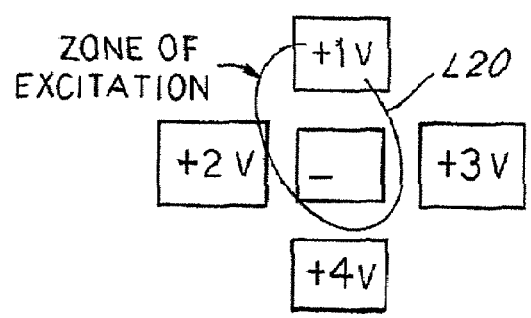

(PATTERNS WITH 4 ELECTRODES)

Figure 23
(PATTERNS WITH SIX ELECTRODES)
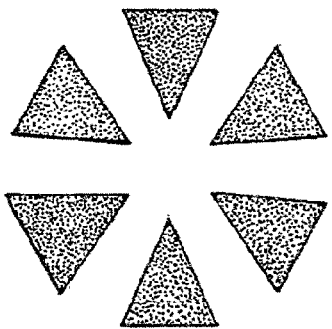
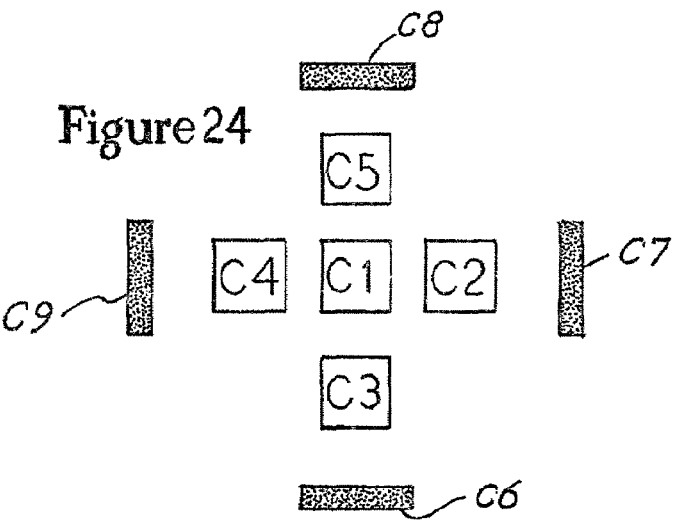
Figure 24
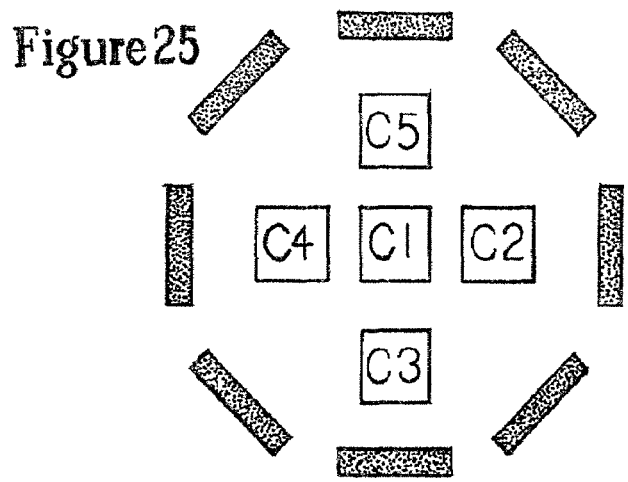
Figure 25

TECHNIQUE FOR ADJUSTING THE LOCUS OF EXCITATION OF ELECTRICALLY EXCITABLE TISSUE WITH PAIRED PULSES

FIELD OF THE INVENTION

This invention relates to deep stimulation of electrically excitable tissue, and more particularly to adjusting the locus at which action potentials are induced in such tissue.

BACKGROUND

Two major practical problems reduce the efficacy of epidural spinal cord stimulation (SCS) for pain control. One is the difficulty of directing the stimulation-induced paresthesia to the desired body part and the other is the problem of disagreeable sensations or motor responses to the stimulation, which reduce the comfortable amplitude range of the stimulation. It is generally agreed that in SCS, for chronic pain, paresthesia should cover the whole pain region. With present stimulation methods and equipment, only highly skilled and experienced practitioners are able to position a stimulation lead in such a way that the desired overlap is reached and desired results (such as deep stimulation) are obtained over time with minimal side effects. It requires much time and effort to focus the stimulation on the desired body region during surgery and, using pulses with single value cathodes, it is difficult to redirect it afterwards, even though some readjustments can be made by selecting a different contact combination, pulse rate, pulse width or voltage.

Redirecting paresthesia after surgery is highly desirable. Even if paresthesia covers the pain area perfectly during surgery, the required paresthesia pattern often changes later due to lead migration, or histological changes (such as the growth of connective tissue around the stimulation electrode) or disease progression. The problem of lead placement has been addressed by U.S. Pat. No. 5,121,754 by the use of a lead with a deformable distal shape. These problems are not only found with SCS, but also with peripheral nerve stimulation (PNS), depth brain stimulation (DBS), cortical stimulation and also muscle or cardiac stimulation.

The era of precise control of electrical fields for excitation of tissue by use of multiple voltages is disclosed in PCT International Publication No. WO 95/19804 (counterpart to Holsheimer et al., U.S. Pat. No. 5,501,703) (the "Holsheimer references"). The Holsheimer references describe the use of electrodes that are "in-line," namely that they are disposed "symmetrically" along a line. The three juxtaposed electrodes have two simultaneous voltages relative to one of them, each with its own amplitude. This approach allows "steering" of the electric fields created by these electrodes. Particularly, the electrical field pattern is adjusted by varying the electrical field generated between those electrodes along that line. The locus of excitation is correspondingly varied with that variation in the electrical field pattern. For example, if a central electrode of three roughly collinear electrodes is a cathode (−) then the outer anodes push the areas of excitation toward the middle, and shield outer areas from excitation. As the anodal pulses are varied in amplitude, the field steers toward the outside.

However, the Holsheimer references disclose a system that requires three electrodes that are optimally spaced symmetrically along a line. It is a serious handicap during the surgical procedure to place these electrodes in the body. Often, a lead such as a paddle is used for mounting the multiple electrodes in the optimally spaced positions. This lead is then inserted within a patient near the tissue to be excited, and electrical excitation is applied to the lead. Unfortunately, placement of a lead such as the paddle within a patient, can be difficult since the paddle can be surgically difficult to manipulate adjacent the spinal cord. Thus, it would be desirable to be able to adjust the locus of excitation in electrically excitable tissue without the use of optimally spaced electrodes.

In addition, the Holsheimer system is limited in that steering is accomplished over a linear path. It would be desirable to adjust the locus of excitation in electrically excitable tissue over a greater area.

SUMMARY

In an aspect of the invention, a method and apparatus is provided to provide and adjust the locus of excitation in electrically excitable tissue using electrodes. In particular, areas of subthreshold excitation may be controlled in order to adjust an area of superposition of such areas of subthreshold excitation. The area of superposition determines the locus of excitation of electrically excitable tissue. Superposition of the first and second subthreshold areas provide deep tissue suprathreshold areas of adjustable locus providing additional action potentials.

In another aspect of the invention, an apparatus includes a generator to provide substantially non-simultaneous pulses to at least two electrodes for inducing action potentials at an adjustable locus of electrically excitable tissue of an organism. A first pulse generates a first action potential area and a first subthreshold potential area.

Additionally, a second pulse generates a second action potential area and a second subthreshold potential area. Superposition of the first subthreshold potential area with the second subthreshold potential area results in a deep tissue suprathreshold potential area of the adjustable locus wherein a third action potential is induced.

In another aspect of the invention, a time delay between the application of the first and second pulses can be varied for a corresponding adjustment in size and location of the suprathreshold potential area. The time delay between the application of the first and second pulses can be measured from the end time of the first pulse to the begin time of the second pulse. Additionally, that delay can be measured as a difference between a first weighted average time of the first pulse and a second weighted average time of the second pulse, or between a first peak time of the first pulse and a second peak time of the second pulse.

These and other features and advantages of the present invention will be better understood by considering the following detailed description of the invention which is presented with the attached drawings.

BRIEF DESCRIPTION OF THE DRAWINGS

These and other advantages and features of the invention will become apparent upon reading the following detailed description and referring to the accompanying drawings in which like numbers refer to like parts throughout and in which:

FIG. 12 shows the suprathreshold potential area generated from application of two pulses to two electrodes where the two pulses having a first time delay between the end of the first pulse and the start of the second pulse.

FIG. 12a shows a deep suprathreshold potential area generated from application of two pulses to two electrodes where the two pulses having a first time delay between the end of the first pulse and the start of the second pulse.

FIG. 13a shows a deep suprathreshold potential area generated from application of two pulses to two electrodes where the two pulses have a second time delay between the end of the first pulse and the start of the second pulse, with the second time delay being greater than the first time delay of FIG. 12.

FIG. 14 shows the suprathreshold potential area generated from application of two pulses to two electrodes where the two pulses have a third time delay between the end of the first pulse and the start of the second pulse, with the third time delay being greater than the second time delay of FIG. 13.

FIG. 15 shows the suprathreshold potential area generated from application of two pulses to two electrodes where the two pulses have a fourth time delay between the end of the first pulse and the start of the second pulse, with the fourth time delay being greater than the third time delay of FIG. 14;

FIGS. 16-25 depict various arrays of electrodes that may be used in accordance with various aspects of the invention.

DETAILED DESCRIPTION

Figure 8:
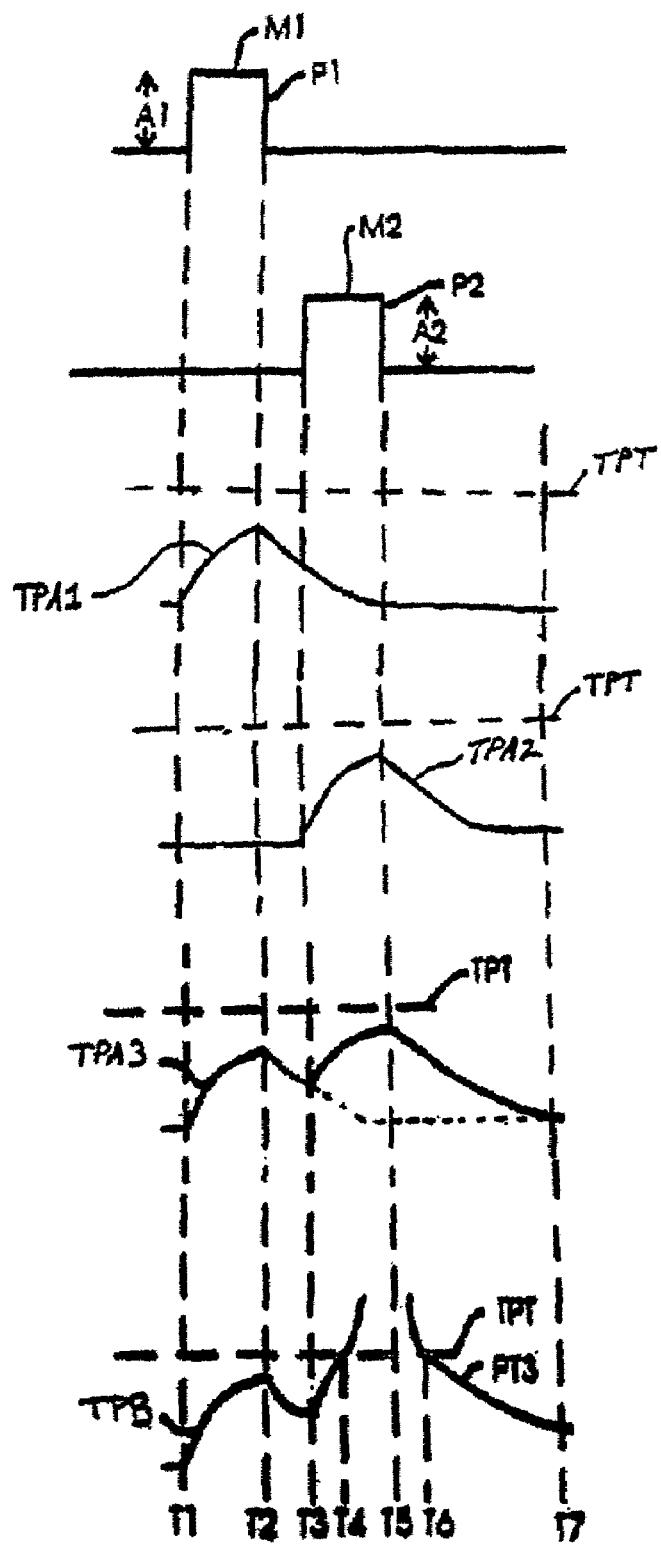
FIG. 8 is a timing diagram showing pulses applied to the first and second electrodes illustrated in FIG. 2 in relationship to the potential changes induced in tissue adjacent the electrodes.

Referring to FIG. 8, a single electrical pulse P1 can cause depolarization near a cathode in electrically excitable tissue which includes neural tissue or muscle tissue. Neural tissue includes peripheral nerves, ganglia, the spinal cord surface, deep spinal cord tissue, deep brain tissue, and brain surface tissue. Muscle tissue includes skeletal (red) muscle, smooth (white) muscle, and cardiac muscle. A locus includes a set of points in three-dimensional space and refers to a volume of cells or parts of cells. Due to the electrical characteristics of both the three-dimensional volume conductor and the membrane properties, the potentials outside and inside a neuron respond to the depolarization, usually with inverse exponential-type increases during the pulse and then attenuation over time after the pulse. The time constant for an isolated neuron membrane typically is 5-15 milliseconds (*Nerve, Muscle and Synapse* by Bernard Katz, circa 1972). For myelinated axons or muscle cells, it may be considerably shorter.

A living cell at any time has a transmembrane potential across its membrane. This transmembrane potential is typically defined as the potential in the inside of the cell with respect to the outside of the cell. At rest, a living cell has a constant transmembrane potential called a resting potential of approximately −60 mV to −90 mV, with the inside of the cell being more negative than outside of the cell. A variety of changes to the environment of the living cell can result in a corresponding change in the transmembrane potential.

A change in the environment that causes the inside of the cell to become less negative is referred to as a "depolarization" of the cell, and depolarization is then a positive change in the transmembrane potential. Similarly, a change in the environment that causes the inside of the cell to become more negative is referred to as a "hyperpolarization" of the cell, and hyperpolarization is a negative change in the transmembrane potential. An example of change in the environment of a living cell is when a voltage pulse is applied near the cell. Depending on the direction of the electric current caused by this stimulation pulse, the pulse can be either depolarizing or hyperpolarizing.

FIG. 8 shows an example pulse P1 that can cause time varying depolarization in a cell, and this depolarization from application of pulse P1 adjacent the cell can result in changes in a transmembrane potential TPA1. A further application of another pulse P2 adjacent the cell results in a portion of the curve TPA2. TPA3 is a superposition of the depolarizations caused by both pulses P1 and P2. The remaining depolarization from the prior application of pulse P1 between times T3 and T7 is shown by the dashed line curve in TPA3.

The transmembrane potential TPA1 is comprised of two components. The first component is the resting potential of the cell. This component is a constant gradient that exists across the membrane of the cell due to steady state ionic concentrations. Added to that first component is the depolarization that results from the application of pulse P1.

Thus, transmembrane potential TPA1 is the sum total of the resting potential with the depolarization effects from application of pulse P1.

The sum total transmembrane potential TPA1 or TPA2 at any time must reach a certain transmembrane potential threshold TPT in order for the electrically excitable cell to get an action potential induced therein. The peak of potential TPA1 or TPA2 is below the transmembrane potential threshold TPT, and thus potential TPA1 or TPA2 can be characterized as a subthreshold potential. As a result, the potential changes from pulses P1 or P2 alone fail to produce an action potential in that cell. Even when pulses P1 and P2 occur with a time delay (T3−T2), the transmembrane potential TPA3 may still not reach the transmembrane potential TPT.

Action potential is an all-or-none, nonlinear phenomenon, caused by opening of sodium gates, inrush of sodium ions, and a delayed opening of potassium gates and a restoration of the membrane potential. In general, a certain amount of charge must be passed at the electrodes (amplitude [Volts]/ resistance [Ohms]× pulse width [time]) in order to cause enough depolarization for an action potential to begin. There is a reciprocal relationship between amplitude and pulse width: the product must reach a certain value before the transmembrane potential threshold is reached. This relationship does not reach the Volts=0 axis. There is a certain minimum voltage needed, called rheobase, before an action potential can happen.

Basic neurophysiological principles, called "electrotonus", show that in any volume of electrically excitable tissue, if two or more depolarizing pulses tending to induce action potentials, each of which alone is insufficient to bring the cells to threshold, arrive closely together in time, at least part of their effect is additive, i.e., the memory of the first pulse is still present when the second pulse arrives. If the sum of the potentials (distorted by resistive and capacitive properties of the surroundings and the cell membranes) can get some cells depolarized to threshold, then an action potential will start in those cells. A reference that explains these principles of "electrotonus" including the creation of subthreshold potentials is *Medical Physiology*, 13th Edition, Vol. 1, by Vernon B. Mountcastle, C. V. Mosby Co., 1974.

Still referring to FIG. 8, the inducement of an action potential in a cell is illustrated by a transmembrane potential TPB reaching the transmembrane potential threshold TPT at time T4. TPB can be characterized as a suprathreshold potential, and the nerve tissue has an action potential started when TPB reaches the transmembrane potential threshold (at time T4). The transmembrane potential TPB is comprised of the constant resting potential and a depolarization that is sufficient enough to push the total transmembrane potential TPB above the transmembrane potential threshold. TPB at time T4 has sufficient depolarization to go above the transmembrane potential threshold because the amplitude of pulse P2 may have either been larger than in the case of the subthreshold transmembrane potential TPA2 or have come soon enough before the memory of the effect of pulse P1 has subsided.

Figure 1:
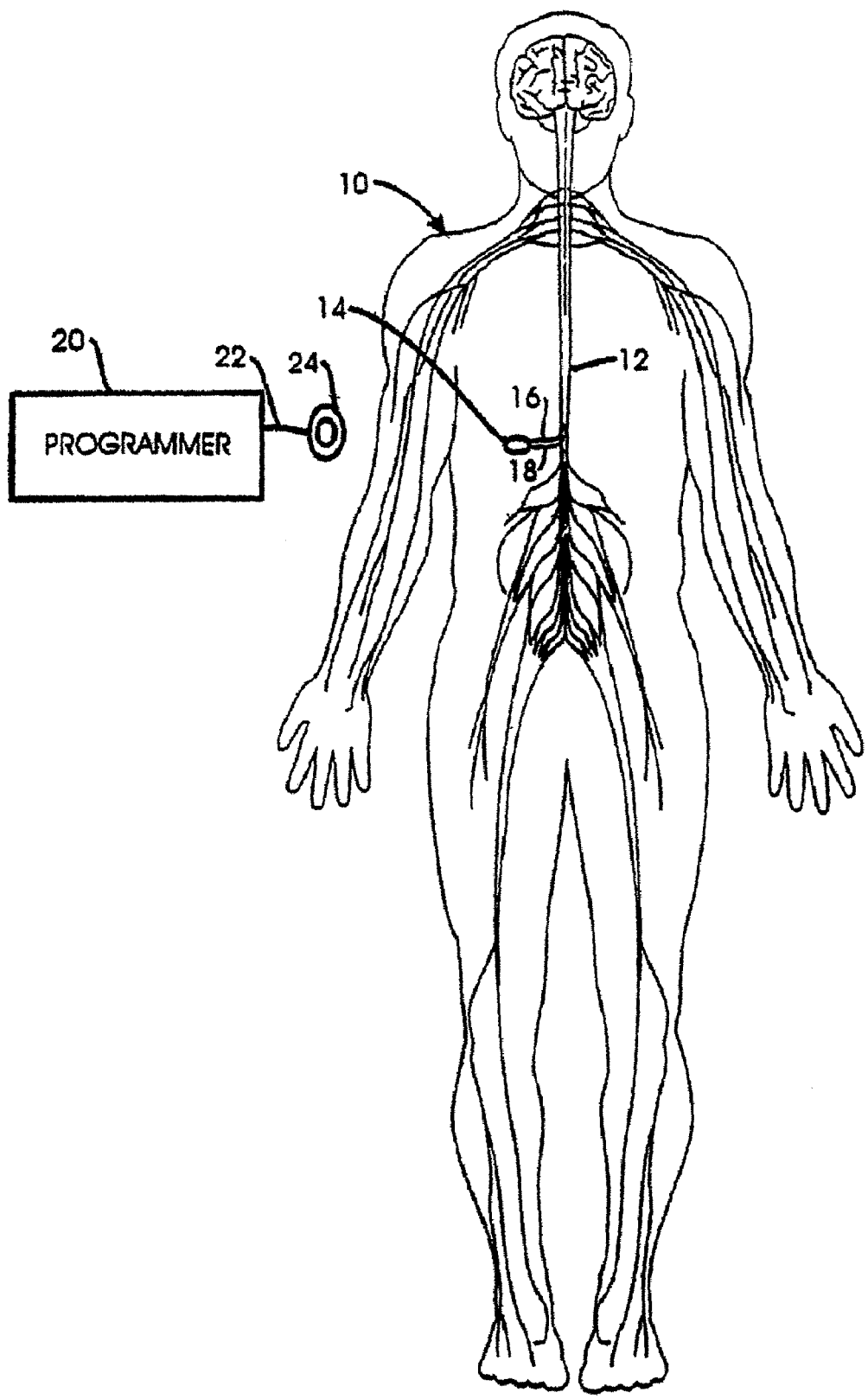
FIG. 1 is a diagrammatic view of a patient in which a preferred form of apparatus for SCS made in accordance with the invention has been implanted.
Figure 2:
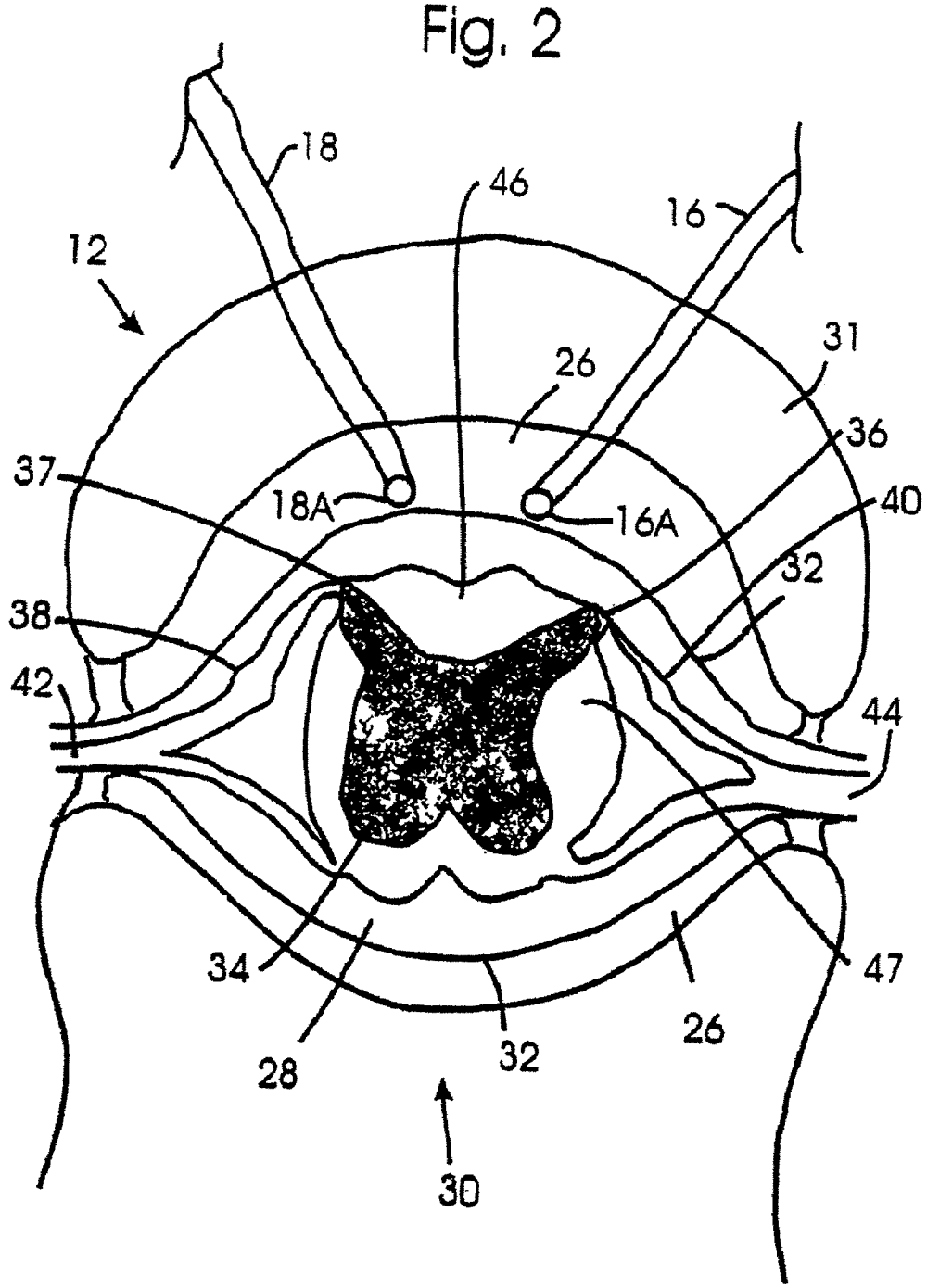
FIG. 2 is a cross-sectional view of an exemplary spinal column showing a typical position at which electrodes made in accordance with the preferred practice of the invention have been implanted in the epidural space.

FIG. 1 is a schematic view of a patient 10 having an implant of a neurological stimulation system employing an aspect of the invention to stimulate spinal cord 12 of the patient. The preferred system employs an implantable pulse generator 14 to produce a number of independent stimulation pulses which are sent to spinal cord 12 by insulated leads 16 and 18 coupled to the spinal cord by electrodes 16A and 18A (FIG. 2). Electrodes 16A and 18A also can be attached to separate conductors included within a single lead.

Implantable pulse generator 14 preferably is a modified ITREL II implantable pulse generator available from Medtronic, Inc. with provisions for multiple pulses occurring either simultaneously or with one pulse shifted in time with respect to the other, and having independently varying amplitudes and pulse widths. This preferred system employs a programmer 20 which is coupled via a conductor 22 to a radio frequency antenna 24. This system permits attending medical personnel to select the various pulse output options after implant using radio frequency communications. While the system employs fully implanted elements, systems employing partially implanted generators and radio-frequency coupling may also be used (e.g., similar to products sold by Medtronic, Inc. under the trademarks X-trel and Mattrix).

FIG. 2 is a cross-sectional view of spine 12 showing implantation of the distal end of insulated leads 16 and 18 which terminate in electrodes 16A and 18A within epidural space 26. The electrodes may be conventional percutaneous electrodes, such as PISCES® model 3487A sold by Medtronic, Inc. Also shown is the subdural space 28 filled with cerebrospinal fluid (cfs), bony vertebral body 30, vertebral arch 31, and dura mater 32. The spine also includes gray matter 34 and dorsal horns 36 and 37 and white matter, for example, dorsal columns 46 and dorsal lateral columns 47.

Stimulation pulses are applied to electrodes 16A and 18A (which typically are cathodes) with respect to a return electrode (which typically is an anode) to induce a desired area of excitation in the spine 12 having nerve tissue capable of producing action potentials. (A cathode has a more negative potential with respect to an anode, and the electrical current caused by the cathode tends to induce an action potential whereas the electrical current caused by the anode tends to inhibit an action potential.) The return electrode, for example a ground or other reference electrode, is also present but is not shown in the cross sectional view of spine 12 because the return electrode is located typically at a different plane from the shown cross section of FIG. 2. For example, the return electrode may be located near a point up or down the line along the spinal column 12 or at a more remote part of the body 10 carrying the spine, such as at the metallic case of the pulse generator 14. Alternatively, more than one return electrode may be present in the body. There can be a respective return electrode for each cathode such that a distinct cathode/anode pair is formed for each cathode.

Referring to FIG. 8, pulse P1 is applied to electrode 18A (FIG. 2) and pulse P2 is applied to electrode 16A (FIG. 2). Pulses P1 and P2 with a magnitude of M1 and M2 have a timing relationship. For optimal operation of the invention with the application of the principle of "electrotonus", pulses P1 and P2 should not overlap in time. For example, the end of pulse P1 at time T2 and the start of pulse P2 at time T3 in FIG. 8 are displaced by a predetermined time period less than 500-2000 microseconds, and preferably less than 50-500 microseconds. Amplitude A1 of P1 is adjustable independently from amplitude A2 of pulse P2. The pulse widths of pulses P1 and P2 also are independently adjustable. Widening the pulse widths of each pulse (i.e., P1 and P2) can also expand the loci of depolarizations, just like increasing amplitude, either voltage or current amplitude.

Figure 9:
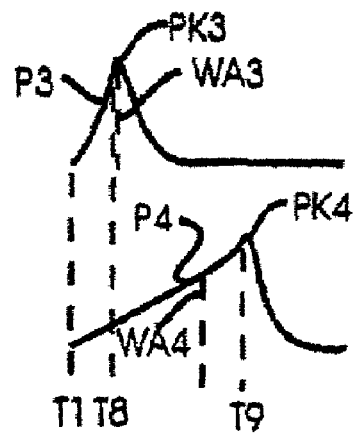
FIGS. 9 and 10 are timing diagrams illustrating alternative forms of pulses applied to the electrodes illustrated in FIG. 2.
Figure 10:
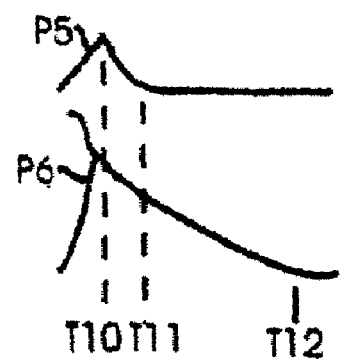

The pulses P1 and P2 also could have other time delay relationships in order to accomplish the goals of various aspects of the invention. Referring to FIG. 9, pulses P3 and P4, having different rise times, could be used. P3 has a rise time from T1 to T8 and P4 has a rise time from T1 to T9. Referring to FIG. 10, pulses P5 and P6, having different fall times, could be used. P5 has a fall time from T10 to T11, and P6 has a fall time from T10 to T12. The weighted average time WA3 of pulse P3 (FIG. 9) is displaced from the weighted average time WA4 of pulse P4 by a predetermined time period of less than 500-2000 microseconds and preferably less than 50-500 microseconds. A weighted average time is the integral of a pulse over the pulse interval divided by the pulse amplitude of the pulse interval. The rise time and fall time of a pulse can affect the weighted average time of the pulse.

Similarly, the peak PK3 of pulse P3 is displaced from the peak PK4 of pulse P4 by a predetermined time period of less than 500-2000 microseconds and preferably less than 50-500 microseconds. The rise time of a pulse can affect the peak time of the pulse. Various aspects of the invention also may be achieved using combinations of the foregoing timing relationships. For example, the time delay between the first pulse and the second pulse can be the time difference between a first weighted average time of the first pulse and a second weighted average time of the second pulse. Alternatively, the time delay can be the time difference between a first peak time of the first pulse and a second peak time of the second pulse.

Figure 3:
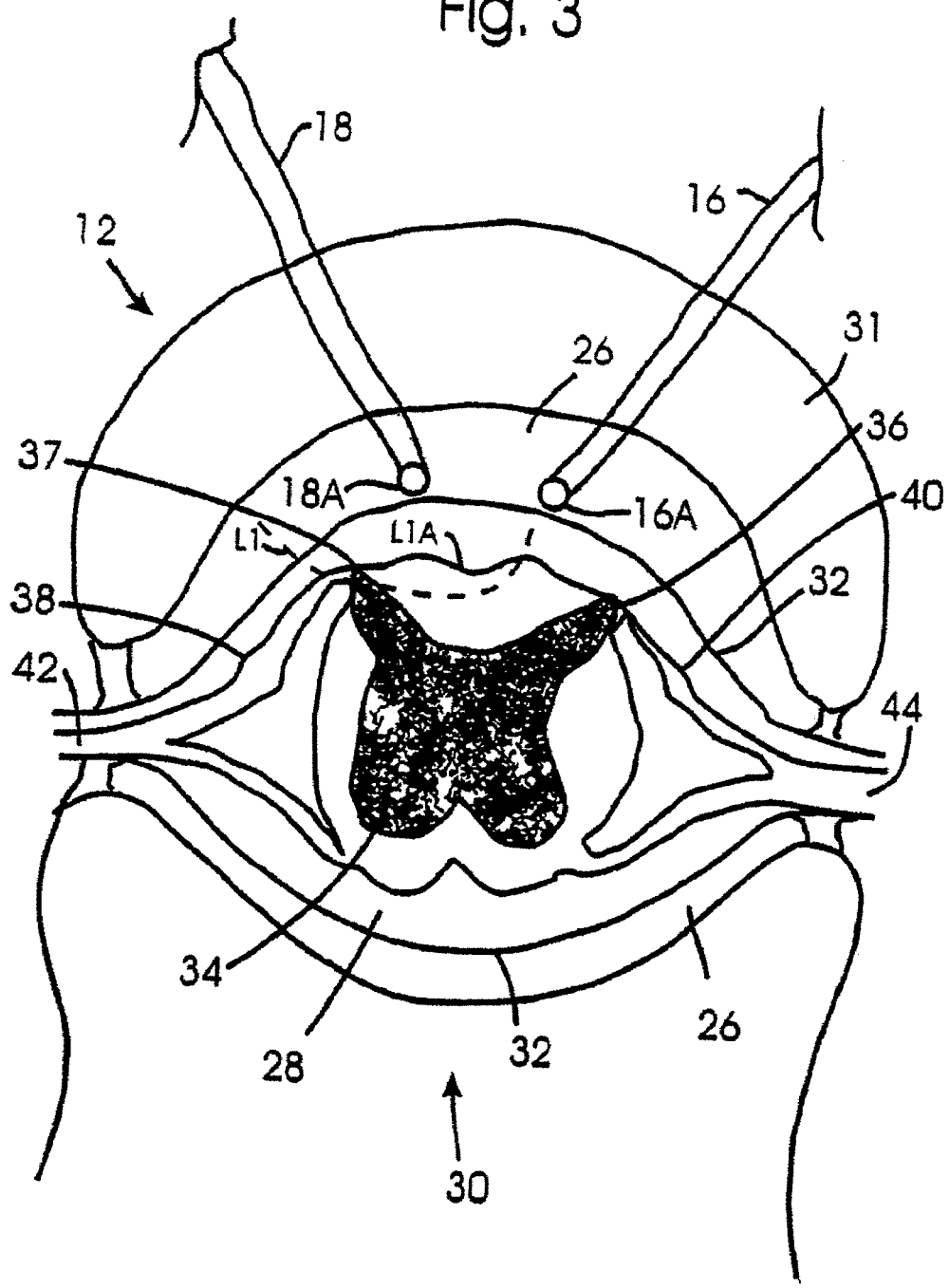
FIG. 3 is a cross-sectional view like FIG. 2 showing locus of potential changes induced in cells of the spinal cord from a pulse applied to a first one of two electrodes.

Referring to FIGS. 3 and 8, line L1 represents the edge of a three-dimensional locus L1A of cells in excitable tissue in which pulse P1 applied to electrode 18A results in a transmembrane potential which can be represented by curve TPA1 of FIG. 8. That transmembrane potential is less than the transmembrane potential threshold TPT for cells of interest in that locus. That transmembrane potential is comprised of a constant resting potential and a depolarization caused by application of pulse P1 to electrode 18A. Thus, locus L1A, which results from pulse P1 being applied to electrode 18A without a recent pulse being applied to electrode 16A is an area having subthreshold potential since TPA1 is less than the transmembrane potential threshold TPT.

Figure 4:
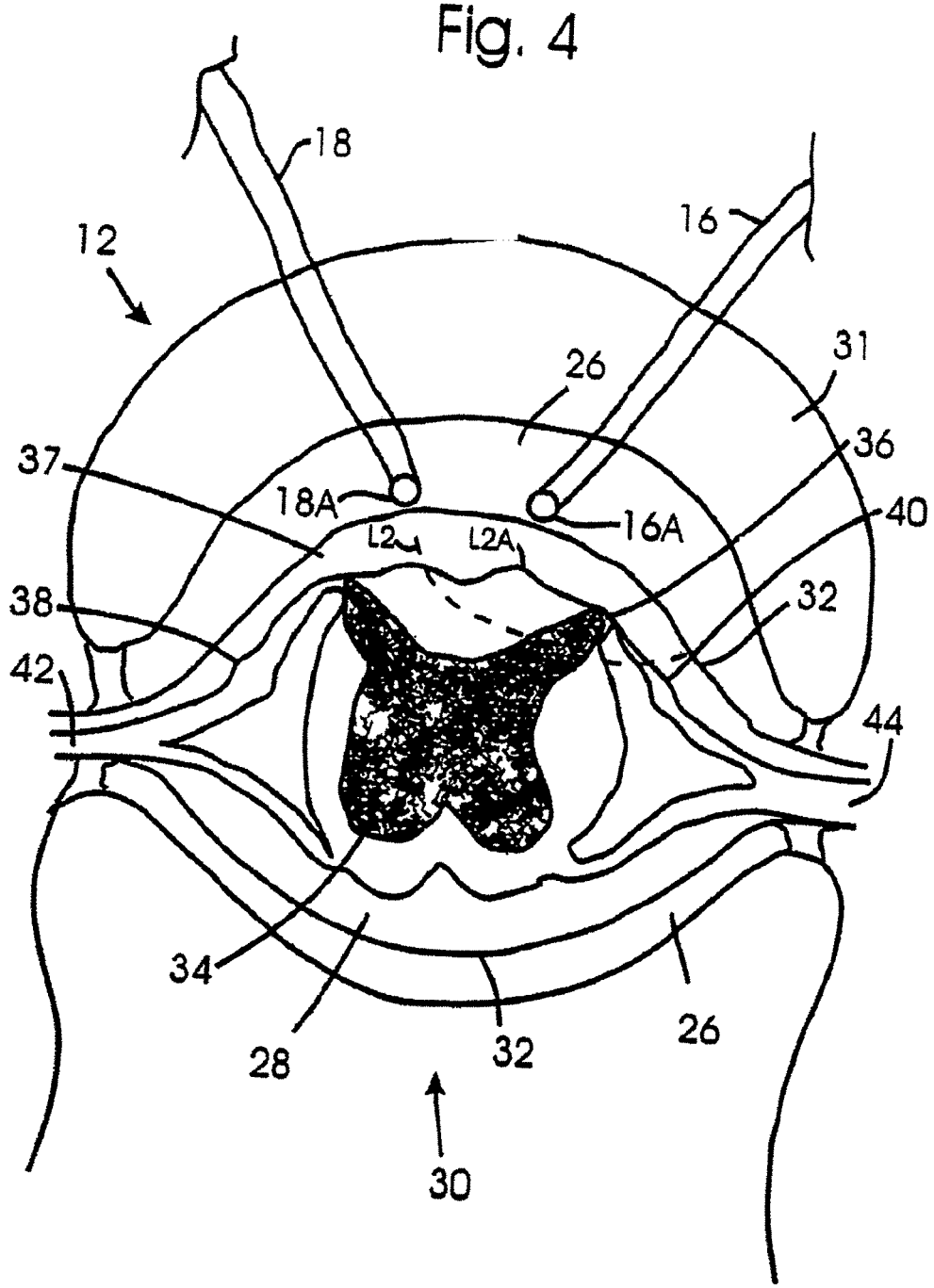
FIG. 4 is a view like FIG. 3 showing the locus of potential changes induced in cells of the spinal cord from the application of a pulse to the second of the electrodes.

Similarly, referring to FIGS. 4 and 8, line L2 represents the edge of another three-dimensional locus L2A in which the application of pulse P2 to electrode 16A results in a transmembrane potential which also can be represented by the transmembrane potential curve TPA2 of FIG. 8. That transmembrane potential is less than the transmembrane potential threshold TPT for cells of interest in that locus. That transmembrane potential is the sum of a constant resting potential and a depolarization potential caused by application of pulse P2 to electrode 16A. Thus, locus L2A, which results from pulse P2 being applied to electrode 16A without a recent pulse being applied to electrode 18A is also an area of subthreshold potential since TPA2 is less than the transmembrane potential threshold TPT.

Figure 5:
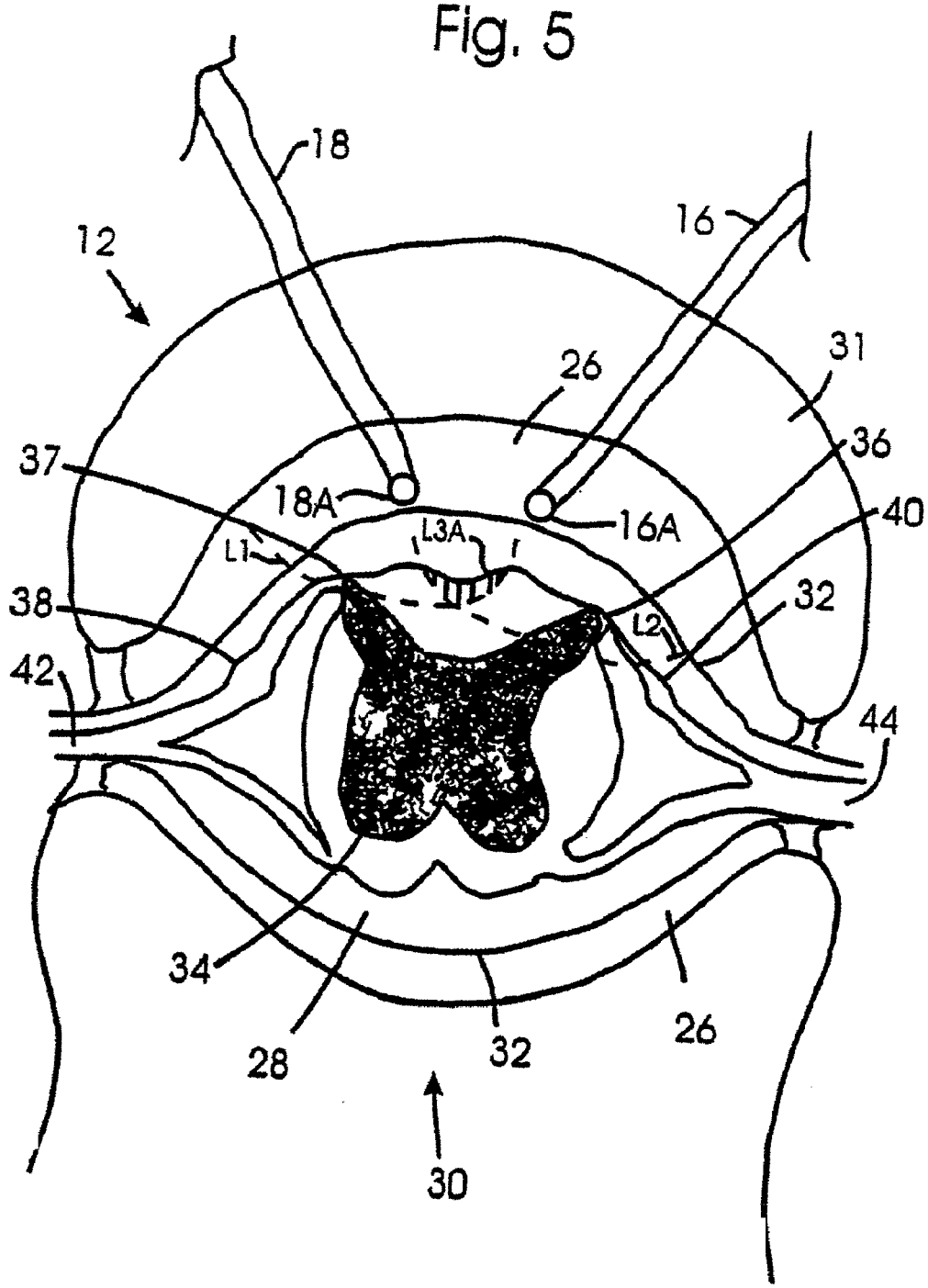
FIG. 5 is a view like FIG. 4 showing the combined loci in the spinal cord at which potential changes are induced from pulses applied to the first and second electrodes.

FIG. 5 illustrates a locus L3A representing the intersection of loci L1A and L2A in which the combined potentials induced in locus L3A from pulses P1 and P2 create an action potential in cells of interest in locus L3A as illustrated by the transmembrane potential TPB in FIG. 8. The total potential in cells in locus L1A outside locus L3A is illustrated by the transmembrane potential TPA1 in FIG. 8. Since TPA1 is lower than the transmembrane potential threshold TPT, the total potential is a subthreshold potential, and there is no action potential created in cells in locus L1A outside L3A. The total potential created in cells in locus in L2A outside L3A is illustrated by transmembrane potential TPA2 in FIG. 8. Again, the total potential is a subthreshold potential, and there is no action potential created in cells in locus L2A outside locus L3A.

The suprathreshold potential induced in cells in locus L3A results from a superposition of the subthreshold potentials TPA1 and TPA2 created in that area by excitation from a pulse applied to electrode 16A and from another pulse applied to electrode 18A. Locus L3A has nerve cells that get action potentials resulting from this suprathreshold potential induced in that locus. The total potential in cells in locus L3A is illustrated by the transmembrane potential TPB of FIG. 8. That transmembrane potential is comprised of the constant resting potential and the superposition of depolarizations from application of pulse P1 to electrode 18A and pulse P2 to electrode 16A.

Figure 6:
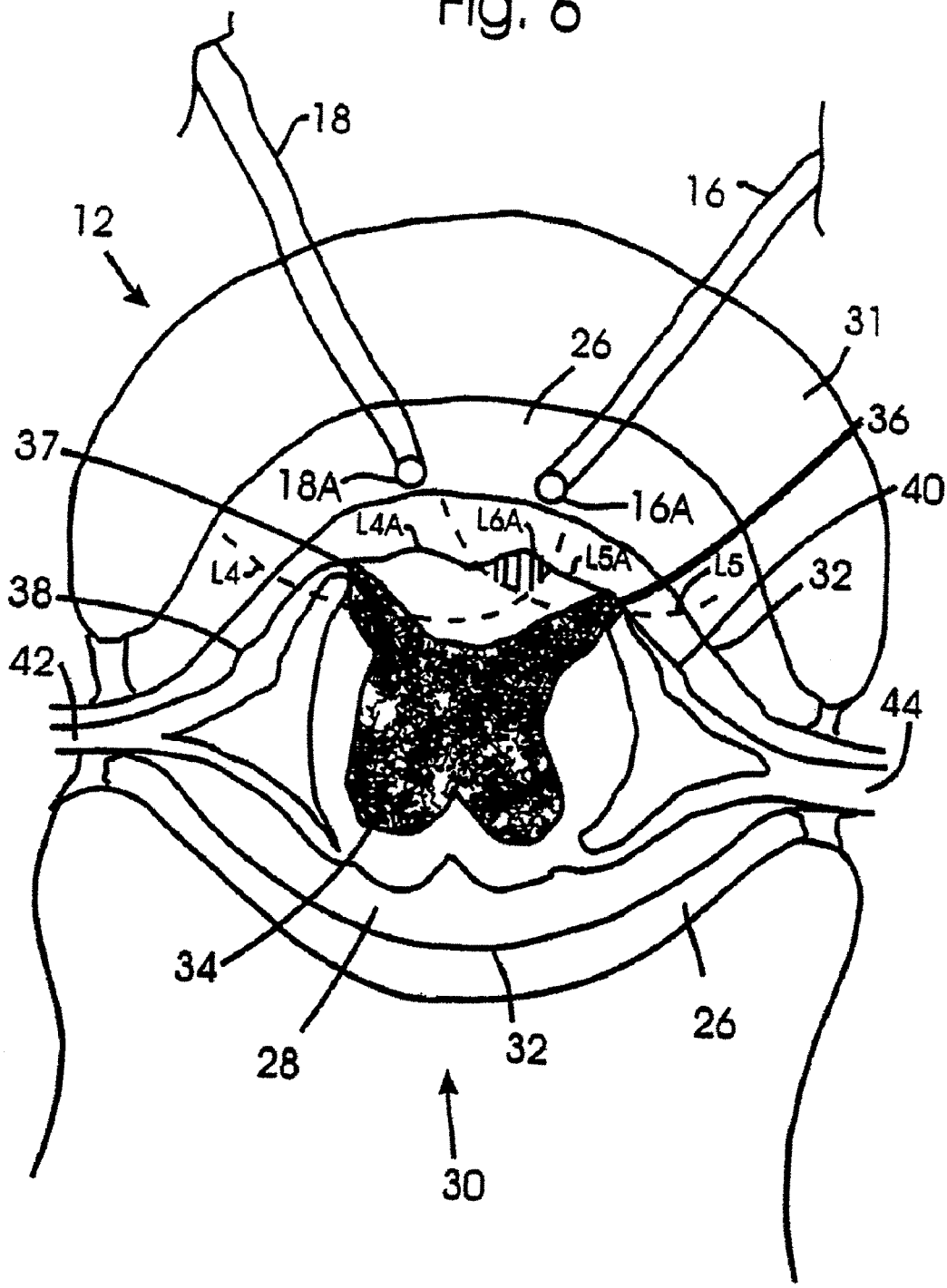
FIG. 6 is a view like FIG. 5 showing the alteration of the loci due to increase in the amplitude of the pulse applied to the first electrode and a decrease in amplitude of the pulse applied to the second electrode.

Referring to FIGS. 6 and 8, line L4 represents the edge of another three-dimensional locus L4A having subthreshold potential resulting from the application of a pulse P1 to electrode 18A having an amplitude greater than amplitude A1. Line L5 represents the edge of another three-dimensional locus L5A having subthreshold potential resulting from the application of a pulse P2 to electrode 16A having an amplitude less than amplitude A2. The intersection of loci L4A and L5A creates a locus L6A in which a suprathreshold action potential results from a superposition of subthreshold potentials created by application of pulses P1 and P2. Locus L6A is moved mostly to the right relative to locus L3A shown in FIG. 5. Action potentials are not induced outside locus L6A since the area outside that locus has subthreshold potentials.

Figure 7:
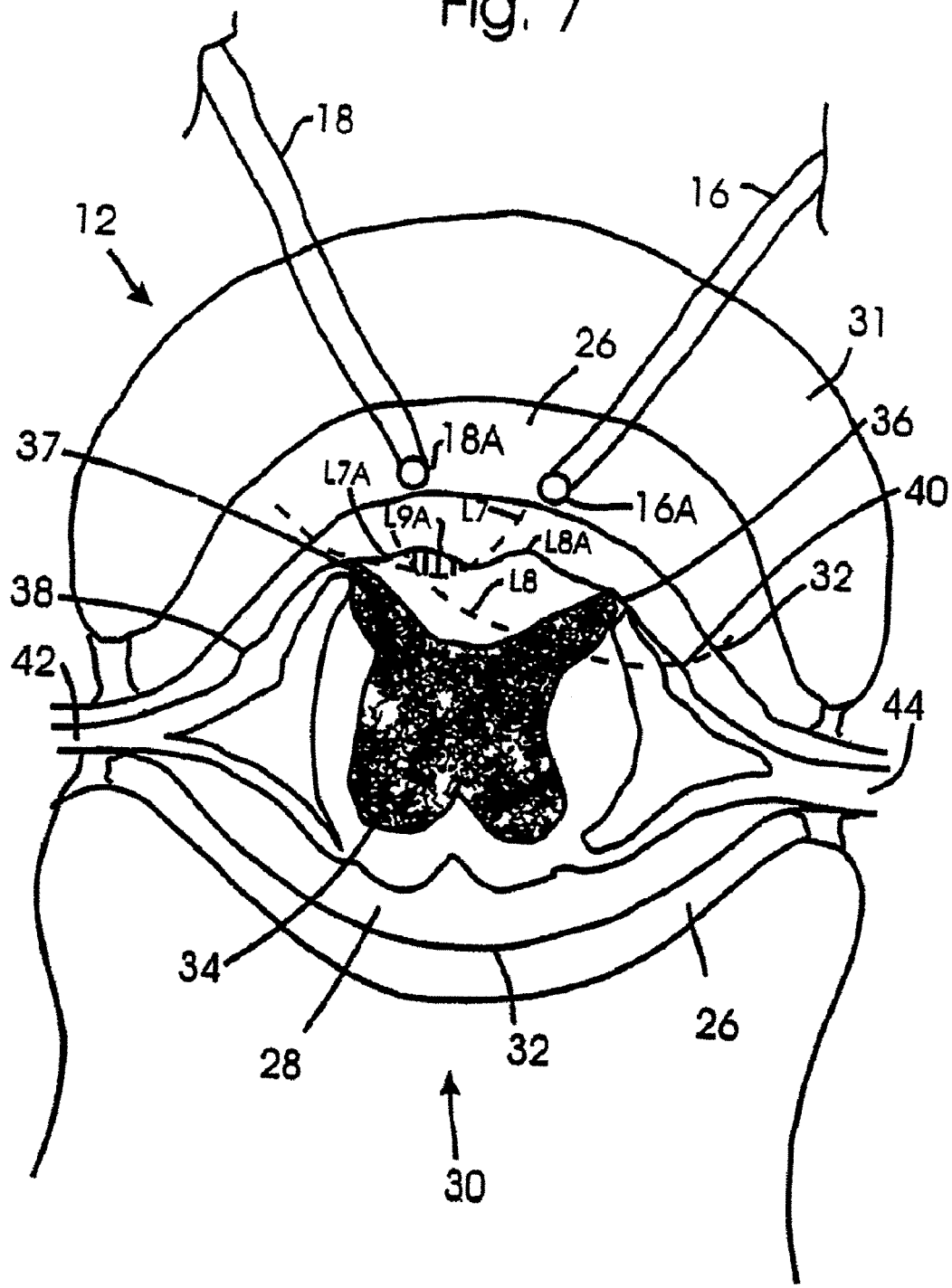
FIG. 7 is a view like FIG. 6 showing the alteration of the loci due to an increase in amplitude of the pulse applied to the second electrode and a decrease in amplitude of the pulse applied to the first electrode.

Referring to FIGS. 7 and 8, line L8 represents the edge of another three-dimensional locus L8A having subthreshold potential resulting from the application of a pulse P2 to electrode 16A having an amplitude greater than amplitude A2. Line L7 represents the edge of another three-dimensional locus L7A having subthreshold potential resulting from the application of a pulse P1 to electrode 18A having an amplitude less than amplitude A1. The intersection of loci L7A and L8A creates a locus L9A in which a suprathreshold action potential is induced from a superposition of subthreshold potentials created by application of both pulses P1 and P2. It will be noted that the locus L9A is moved to the left compared with locus L3A shown in FIG. 5. Action potentials are not induced outside locus L9A since the area outside that locus has subthreshold potentials.

A benefit of utilizing the neurophysiological principle of "electrotonus" is that the area of suprathreshold potential can be controlled by varying the time delay between application of the two pulses to each respective driven electrode for creating the areas of subthreshold potential. Referring to FIG. 8, this time delay can be the time period between the end of pulse P1 at time T2 and the start of pulse P2 at time T3.

Principles of "electrotonus" indicate that a potential for any nerve cell decays with a RC time constant after a stimulation pulse has been applied to that nerve cell. R is a resistive value determined by the resistive characteristic for that nerve cell, and C is a capacitive value determined by the capacitive characteristic for that nerve cell.

Because of this memory effect of electrotonus, the transmembrane potential created within a nerve cell by a pulse starts to decay at the end of the excitation pulse, and this transmembrane potential is a function of time. By taking advantage of this time variation of the transmembrane potential, the area of suprathreshold potential can be adjusted by correspondingly varying the time delay between the pulses that are applied to two electrodes that each produce a subthreshold area.

This benefit is further illustrated in FIGS. 12-15 where elements similar to elements in the prior figures are labeled with the same numeric label. FIG. 12 illustrates the case where the pulses applied to the two cathodes follow closely in time. Element 12 is a simplified illustration of electrically excitable tissue such as spinal cord tissue. Pulse P2 immediately follows after the end of pulse P1, and the time delay between the end of pulse P1 at T2 and the start of pulse P2 at T3 is small in this case.

Line L10 represents the isopotential line defining a subthreshold area L10A created by application of pulse P1 at electrode 18A. Line L11 represents the isopotential line defining another subthreshold area L11A created by application of pulse P2 at electrode 16A. (A return electrode is not shown in FIGS. 12-15 since that electrode is typically located on a different plane from the shown spinal cord tissue 12 or on a more remote location on the body carrying the tissue 12 such as at the metallic case of the pulse generator 14 of FIG. 1.) Each isopotential line varies with time and progresses away from the electrode producing that isopotential line during the application of a pulse to that electrode and recedes back toward that electrode after the completion of the pulse by the principle of "electrotonus". In FIG. 12, the isopotential lines L10 and L11 are what result at the end of pulse P2 at time T4. These individual subthreshold areas by themselves do not have sufficient potential changes to induce an action potential within tissue 12. However, a superposition of the subthreshold potential areas at time T4 creates an area L12A of suprathreshold potential that is greater than the transmembrane potential threshold such that nerve cells within that area have an action potential induced therein.

FIG. 12a illustrates another aspect of the invention in which a deep stimulation of the dorsal column may be accomplished without inducing action potentials in the dorsal horns 36 and 37, gray matter 34 or dorsal lateral columns 47 or dorsal root ganglia 38 and 40. In FIG. 12a the two pulses P1 and P2 may be greater in amplitude than the corresponding pulses illustrated in FIG. 12.

In FIG. 12a, pulses applied to at least two cathodes follow closely in time. Element 12 is a simplified illustration of electrically excitable tissue such as spinal cord tissue. Pulse P2 immediately follows after the end of pulse P1, and the time delay between the end of pulse P1 at T2 and the start of pulse P2 at T3 is small in this case.

Line L100 represents the isopotential line defining an action potential area L100A created by application of pulse P1 at electrode 18A. Line L111 represents the isopotential line defining another action potential area L111A created by application of pulse P2 at electrode 16A. Line L20 represents the isopotential line defining a subthreshold area L20A created by application of pulse P1 at electrode 18A. Line L21 represents the isopotential line defining another subthreshold area L21A created by application of pulse P2 at electrode 16A.

Each isopotential line varies with time and progresses away from the electrode producing that isopotential line during the application of a pulse to that electrode and recedes back toward that electrode after the completion of the pulse by the principle of "electrotonus".

In FIG. 12a, the isopotential lines L20, L21, L100, and L111 are what results at the end of pulse P2 at time T4.

In FIG. 12a, electrode 18A may have amplitude such that at least one action potential is generated in zones or areas numbered 1, 2, and 8 of the spinal cord tissue. Furthermore, a subthreshold area of activation may be produced in nearby spinal cord tissue resulting from the application of pulse P1 to electrode 18A. The areas of subthreshold activation may include nearby zones 3, 4, and 5.

Electrode 16A may also have amplitude such that at least one action potential is generated in zones numbered 1, 3, and 7. This may cause two action potentials to be produced in zone 1, if the two pulses P1 and P2 are far enough apart (where the second pulse is not in the neuron's refractory period from the first pulse). A wider area comprised of zones 2, 4, and 6 may also comprise areas of subthreshold activation in response to excitation by electrode 16A.

When the amplitudes of P1 and P2 are both of sufficient magnitude, there may be one action potential produced in each of zones 8, 2, 1, 3, and 7. Zone 1 may represent a superposition of the subthreshold potential areas at time T4 which creates an area L12A of suprathreshold potential that is greater than the transmembrane potential threshold such that nerve cells within that area have an action potential induced therein.

Furthermore, zone 4 which represents deep spinal cord tissue excitation may also have an action potential produced, if pulses P1 and P2 add up by electrotonus to generate an action potential. Zone 4 is especially deep into the spinal cord tissue and may be positioned midway between the two electrodes.

Those skilled in the art will realize that all electrodes may stimulate the surface at high enough amplitudes. Also, by electrotonus a deep area may be activated, without activation of neighboring zones such as zones 5 and 6. Furthermore, the stimulation of zone 4 may be stimulated with paired pulses that are close together in time, with appropriate amplitudes and/or pulse widths. If all pulses are simultaneous, zones 4, 5, and 6 may be affected nearly equal. If the pulses have different pulse widths, and do not overlap in part of their time, a similar area of deep activation may also be realized.

Figure 13:
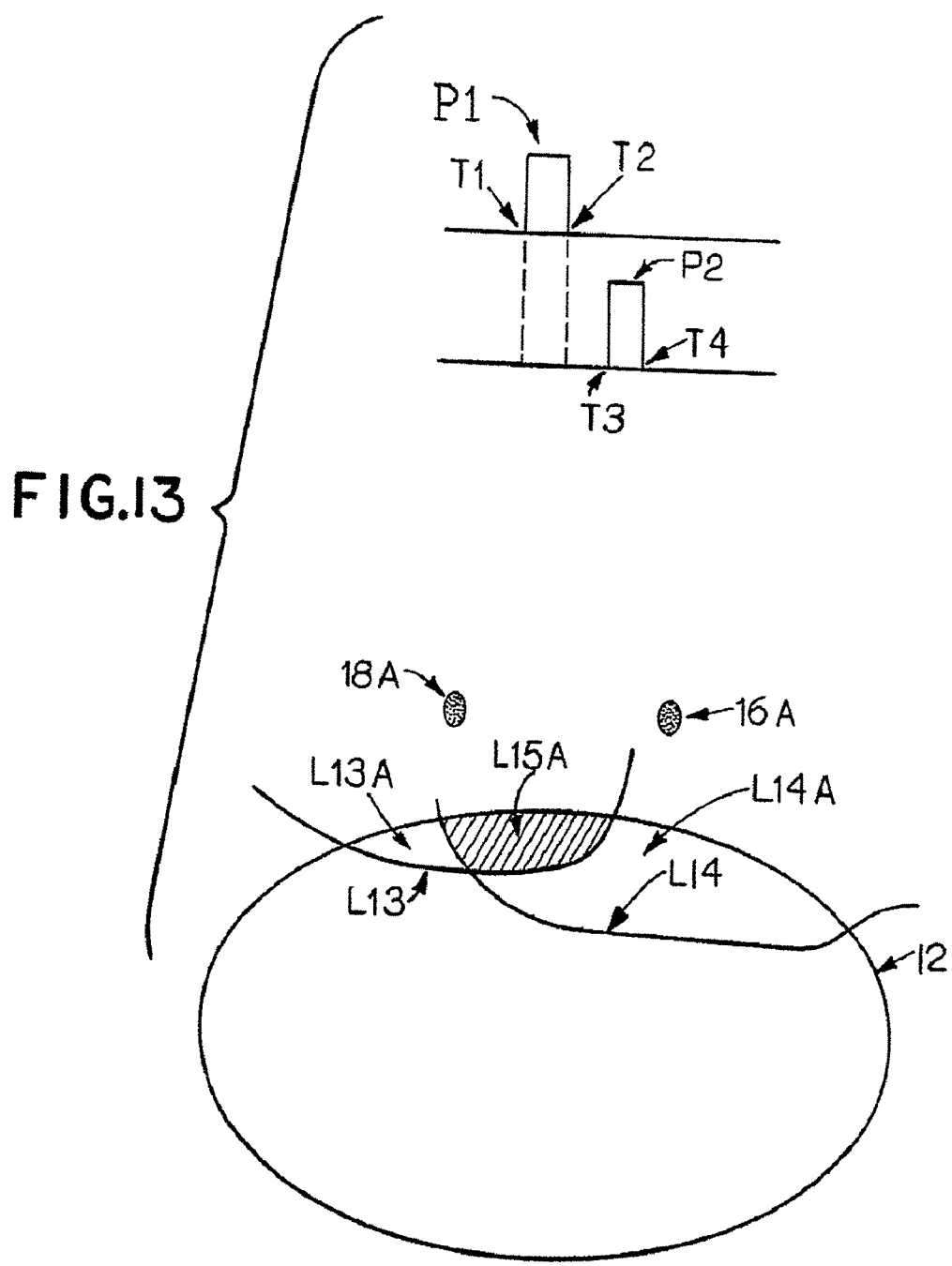
FIG. 13 shows the suprathreshold potential area generated from application of two pulses to two electrodes where the two pulses have a second time delay between the end of the first pulse and the start of the second pulse, with the second time delay being greater than the first time delay of FIG. 12.

FIG. 13 shows a case where the two pulses P1 and P2 are more separated in time than the cases illustrated in FIGS. 12 and 12a. The transmembrane potentials in FIG. 13 that are created in electrically excitable tissue 12 are those that remain at the end of pulse P2 at time T4. By that time, the application of pulse P1 was already completed at time T2. Isopotential line L13 defines the subthreshold area L13A that remains from the application of pulse P1 to electrode 18A by time T4. Isopotential line L14 defines the subthreshold area L14A that is created by application of pulse P2 to electrode 16A by time T4.

These individual subthreshold areas by themselves do not have sufficient potential changes to induce an action potential. However, a superposition of the subthreshold potential areas creates an area L15A of suprathreshold potential that is greater than the transmembrane potential threshold such that nerve cells within that area have an action potential induced therein. Note that the area of suprathreshold potential L15A of FIG. 13 differs from the area of suprathreshold potential L12A of FIG. 12 because of the larger time delay between the end of pulse P1 at T2 and the start of pulse P2 at T3 in FIG. 13 than in FIG. 12.

FIG. 13a illustrates another aspect of the invention in which a deep stimulation of the dorsal column may be accomplished with two pulses P1 and P2 that are more separated in time than the cases illustrated in FIGS. 12 and 12a.

Line L130 represents the isopotential line defining an action potential area L130A created by application of pulse P1 at electrode 18A. Line L140 represents the isopotential line defining another action potential area L140A created by application of pulse P2 at electrode 16A. Line L30 represents the isopotential line defining a subthreshold area L30A created by application of pulse P1 at electrode 18A. Line L31 represents the isopotential line defining another subthreshold area L31A created by application of pulse P2 at electrode 16A.

Each isopotential line varies with time and progresses away from the electrode producing that isopotential line during the application of a pulse to that electrode and recedes back toward that electrode after the completion of the pulse by the principle of "electrotonus".

In FIG. 13a, the isopotential lines L130, L30, L140, and L31 are what result at the end of pulse P2 at time T4.

In FIG. 13a, electrode 18A may have amplitude such that at least one action potential is generated in zones 1, 2, and 8 of the spinal cord tissue. Furthermore, a subthreshold area of activation may be produced in nearby spinal cord tissue resulting from the application of pulse P1 to electrode 18A. The areas of subthreshold activation may include nearby zones 3, 4 and 5.

Electrode 16A may also have amplitude such that at least one action potential is generated in zones numbered 1, 3, and 7. This may cause two action potentials to be produced in zone 1, if the two pulses P1 and P2 are far enough apart (where the second pulse is not in the neuron's refractory period from the first pulse). A wider area comprised of zones 2, 4, and 6 may comprise areas of subthreshold activation in response to excitation by electrode 16A.

When the amplitudes of P1 and P2 are both of sufficient magnitude, there may be one action potential produced in zones 8, 2, 1, 3, and 7. Zone 1 may represent a superposition of the subthreshold potential areas at time T4 which creates an area L15A of suprathreshold potential that is greater than the transmembrane potential threshold such that nerve cells within that area have an action potential induced therein.

Furthermore, zone 4 which represents deep spinal cord tissue may also have an action potential produced, if pulses P1 and P2 add up by electrotonus to generate an action potential.

Zone 4 is especially deep into the spinal cord tissue.

As stated above with respect to FIG. 12a, by electrotonus a deep area may be activated, without its neighboring areas, 5 and 6. The stimulation of zone 4 may be stimulated with paired pulses that are close together in time, with appropriate amplitudes and/or pulse widths. If all pulses are simultaneous, zones 5, 4 and 6 may be affected nearly equal. If the pulses have different pulse widths, and do not overlap in part of their time, a similar area of deep activation may also be realized.

Similarly, FIG. 14 shows a case where the two pulses P1 and P2 are still even more separated in time than those of FIG. 13. FIG. 14 shows the isopotential lines that are created by pulses P1 and P2 at the end of pulse P2 at time T4. The isopotential line L16 defines the subthreshold area L16A created by the application of pulse P1 at electrode 18A by time T4, and the isopotential line L17 defines the subthreshold area L17A created by the application of pulse P2 at electrode 16A by time T4.

The individual subthreshold areas within isopotential lines L16 and L17 by themselves do not have sufficient potential changes to induce an action potential. However, a superposition of subthreshold potential areas creates an area L18A of suprathreshold potential that is greater than the transmembrane potential threshold such that nerve cells within that area have an action potential induced therein. Note that because of the larger delay between pulses P1 and P2, isopotential line L16 has receded further toward electrode 18A by the end of pulse P2 at time T4, and the area L18A of suprathreshold potential has decreased and has shifted more toward electrode 18A.

FIG. 15 shows a case where pulse P1 and P2 have a time delay sufficiently far enough such that no area of suprathreshold potential is created within the electrically excitable tissue 12. Isopotential line L19 is the result of application of pulse P1 at electrode 18A by the end of pulse P2 at time T4, and isopotential line L20 is the result of application of pulse P2 at electrode 16A by time T4. Because of the large delay between pulses P1 and P2, isopotential line L19 has receded so far back toward electrode 18A that there is no area of superposition of the two subthreshold areas created by isopotential lines L19 and L20 within tissue 12.

The ability to move the locus in which action potentials are induced by controlling the area of superposition of subthreshold potential areas is an important feature. In many therapies, it is important to prevent action potentials being induced in gray matter 34 or dorsal horns 36 and 37, dorsal roots 38 and 40, dorsal lateral columns 47 or peripheral nerves 42 and 44 in order to minimize the possibility of causing pain, motor effects, or uncomfortable paresthesia. With the described techniques, the locus in which action potentials are induced (e.g., L3A, L6A, L9A, L12A, L15A, or L18A) can be manipulated to a desired area of the dorsal columns 46 without inducing action potentials in dorsal horns 36 and 37, gray matter 34 or dorsal lateral columns 47 or dorsal root ganglia 38 and 40. Moreover, the ability to move the locus in which action potentials are induced drastically reduces the accuracy necessary for surgically implanting electrodes 16A and 18A, and may eliminate the need for surgical lead revisions.

Another advantageous result from being able to determine the locus of excitation by controlling the area of suprathreshold potential from superposition of subthreshold potential areas is that the location of the two driven electrodes 16A and 18A and the return electrode with respect to each other is not critical to the practice of this invention.

In contrast to the invention disclosed by Holsheimer et al. in U.S. Pat. No. 5,501,703, the two driven electrodes and the return electrode in various aspects of the invention are not optimally spaced in line with respect to each other. In fact, the return electrode of may be located remotely from the driven electrodes 16A and 18A near a point up or down the spinal column or another part of the body carrying the spine being excited.

Alternatively, there may be more than one return electrode within the body.

Figure 11:
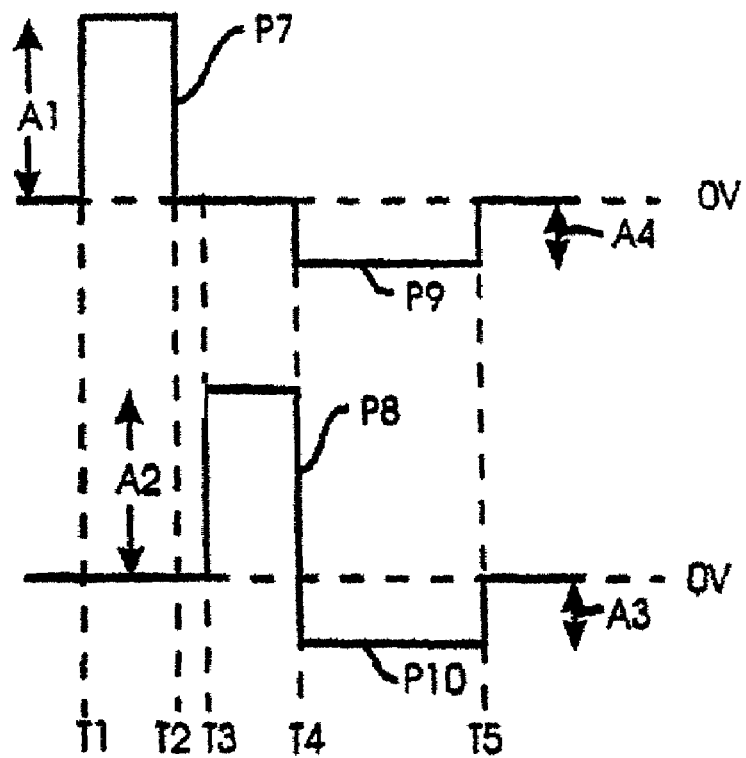
FIG. 11 is a timing diagram illustrating a preferred form of pulses applied to the electrodes shown in FIG. 2.

FIG. 11 illustrates a preferred timing relationship between pulse P7 applied to electrode 18A and pulse P8 applied to electrode 16A. Currently available pulse generators use a biphasic pulse to insure no net direct current flows into the tissue. This is known as charge-balanced pulsing, and is accomplished by driving the pulse negative for a duration of time. For example, in FIG. 11, pulse P8 has a net charge delivered proportional to A2*(T4−T3). This injected charge is balanced by the negative pulse P10, whose charge is proportional to A3*(T5−T4), where A3<<A2 and (T5−T4)>> (T4−T3). Similar principles apply even if the first and second pulses are not of constant amplitude.

In a preferred embodiment, pulse P7 may be generated with a trailing negative pulse P9 from time T4 to time T5, so that the output on electrode 18A is substantially at neutral or 0 potential until the termination of pulse P8 at time T4. Having this delay in charge balancing prevents the loss of potential in adjacent tissue that otherwise would occur if pulse P9 immediately followed pulse P7 and overlapped with pulse P8, thus offsetting the benefit of pulse P8. At time T4 both negative pulses P9 and P10 begin in order to maintain the charge balance in tissue adjacent to the respective electrodes 18A and 16A.

In another embodiment of the invention, an array of electrodes may be used to more finely control the shape of the field of excitation. These electrodes provide multi-channel stimulation of the desired treatment area. Multi-channel stimulation generally refers to the stimulation of several sites at differing pulse parameters including, for example and without limitation, pulse amplitude, pulse width, pulse frequency, pulse shape, pulse rise, pulse fall, pulse peak, and pulse polarity. These pulses may be either voltage or current pulses. For example, if one site receives a voltage or current pulse, and then another site gets a pulse at the same time, an overlapping time, or a separate time. The stimulation and steering techniques discussed above may be used to achieve suprathreshold potentials within the desired treatment areas. The field of excitation may be created and controlled using any number of techniques, including but not limited to, simultaneous pulses of two cathodal amplitudes and one anode, paired (delayed) pulses using two or more electrodes, a combination of simultaneous and paired (delayed) pulses among various electrodes, and conventional full polarity pulses of anodes and cathodes. Each of these techniques are discussed herein in further detail.

FIG. 16 shows a way to perform two-dimensional steering using an array 1600 of electrodes. These electrodes may be placed on a paddle lead or may be positioned across three adjacent percutaneous leads. Array 1600 may include a central cathode C1 and up to four surrounding anodes C2-C5. Simultaneous anodal pulses can then be delivered, each with their own potential, to the surrounding electrodes C2-C5. Advantageously, the electric field may be steered in any number of directions over a 2-dimensional space. As exemplified in FIG. 17, the effect may be steered from left to right by using electrodes C1, C2 and C4 and turning off electrodes C3 and C5. Further, as exemplified in FIG. 18, the effect may be steered from top to bottom by using electrodes C1, C3 and C5. FIG. 19 illustrates a method to shield activation of cells in a lower direction and to maintain the field of excitation in the middle and slightly upward. The field of excitation L19 is skewed by using only anodal electrodes C2-C4, where electrode C3 is stronger in voltage than electrodes C2 and C4. FIG. 20 illustrates steering of field L20 along a diagonal by using surrounding electrodes C2-C5 but with varying voltages.

As shown in FIG. 21, central electrode C1 may also be eliminated altogether. In this case, one of the remaining electrodes, say C2 is the most cathodal (−), and the remaining three electrodes C2-C4 can be programmed to have three equal or different anodal voltages to provide the necessary steering of the field L21. Although the currents from electrode C2 move off in the other direction in a less controlled manner, this embodiment advantageously avoids current waste that would be present with a nearby central cathode C1.

Figure 22:
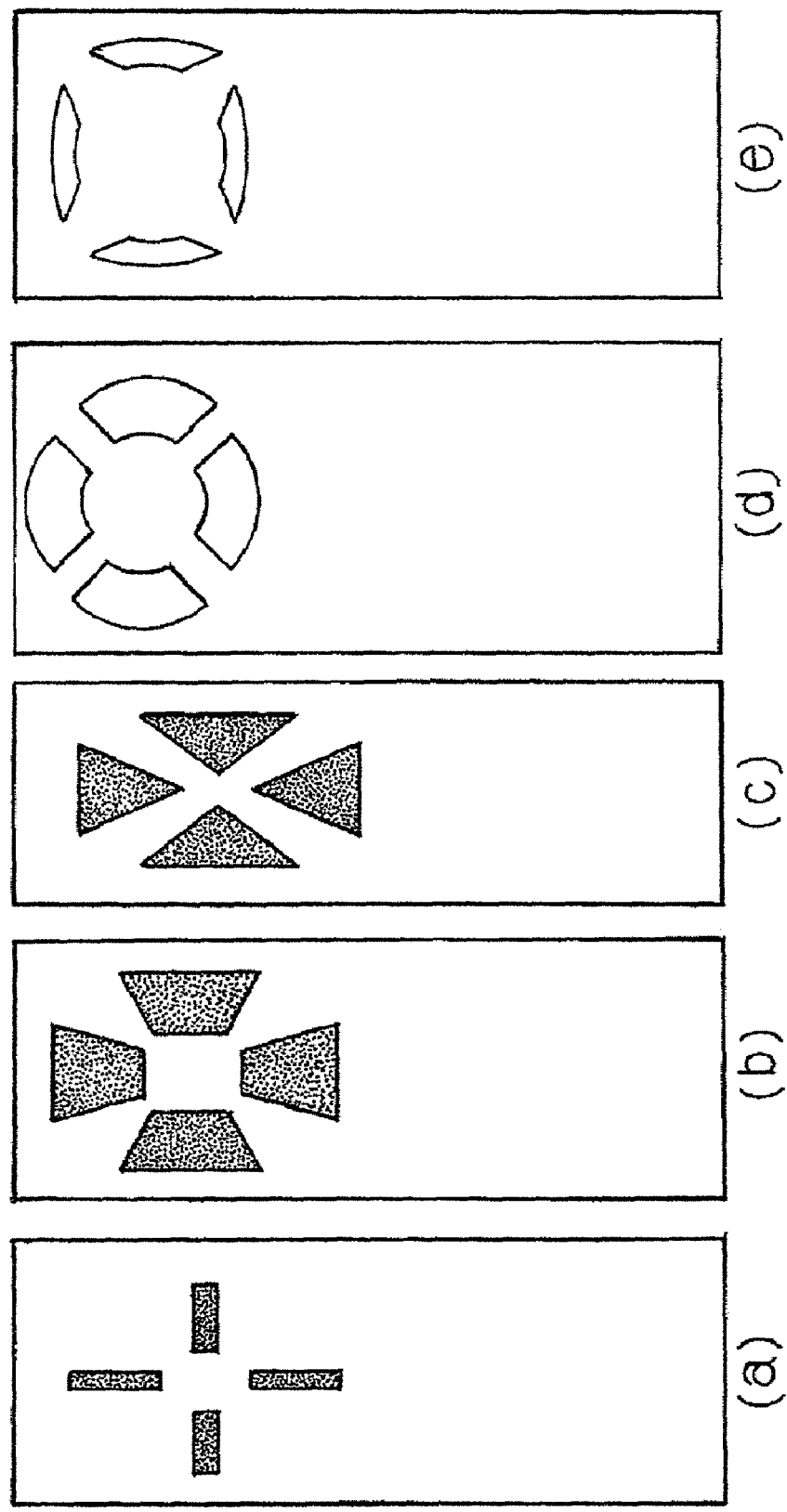

FIGS. 22(a-e) shows a number of electrode shape configurations that may prevent unnecessary shorting of currents in the epidural space, or help direct energy into certain patterns. FIG. 22(a) has greater efficiency since the electrodes are relatively far from each other. FIGS. 22(b and c) depict electrodes having relatively larger surface areas, thereby reducing resistance and allowing for higher currents. FIG. 22(d) has four electrodes farther apart forming a ring. FIG. 22(e) depicts relatively smaller electrodes that are further apart from each other to increase efficiency and minimize shunting of current between the electrodes.

FIG. 23 illustrates a similar concept but with 6 electrodes in a ring pattern to provide greater control of the direction of the electric field. Here, up to five or more anodal voltage levels may be used (if one is most cathodal), or up to six cathodal voltage levels may be used (if there is one distant anode, say, on a power source case). Those skilled in the art will appreciate that even other electrode configurations can be used together with more simultaneous pulses or varying amplitudes. Delivery of subthreshold pulses at various times may result in a two-dimensional locus of superactivation.

FIG. 24 shows the initial cross-pattern of five electrodes C1-C5 with some outer electrodes C6-C9. If any of the ring of electrodes C2-C5 is made a cathode, electrode C1 may be turned off and one or more outer electrodes C6-C9 can be made anodal to help maintain the field of excitation bounded on that side. FIG. 25 is yet another embodiment having five or more electrodes in an outer ring that could be anodal to contain the electric field toward the center.

Advantageously, these 2-dimensional configurations may be used to create suprathreshold potential areas as discussed above. Stimulation may be provided using a two-dimensional array of electrodes and configuring a range of anode/cathode relationships from the array. Moreover, simultaneous pulsing may be achieved by applying pulses of varying amplitudes to a selected group of cathodes in the array.

The advantages of various aspects of the invention described herein can be generalized to applications for exciting any electrically excitable tissue within any organism, in addition to such tissue within a spine. Particularly, the same techniques may be used for intraspinal, cortical, deep brain, peripheral nerve, heart or other muscle or organ stimulation as well. Further, the fields to be generated might have either constant current or constant voltage sources. Moreover, aspects of the invention may be generalized to using more than two cathodal electrodes to generate more than two subthreshold areas to be superposed in generating the suprathreshold potential area. Accordingly, the forgoing description is by way of example only and is not intended to be limiting.

I claim:

1. An apparatus including at least two electrodes for inducing action potentials at an adjustable locus of electrically excitable tissue of an organism, comprising in combination:
    a first electrode selected from the at least two electrodes, the first electrode capable of being driven with a first pulse, the first pulse having a pulse parameter to generate a first action potential area and a first subthreshold potential area;
    a second electrode selected from the at least two electrodes, the second electrode capable of being driven with a second pulse, the second pulse having a pulse parameter to generate a second action potential area and a second subthreshold potential area; and
    a generator configured to provide the first and second pulses to the first and second electrodes to create a steerable electric field,
    the generator providing substantially non-simultaneous pulses to the first and second electrodes and wherein the superposition of the first subthreshold potential area with the second subthreshold potential area results in a deep tissue suprathreshold potential area of the adjustable locus wherein a third action potential is induced.

2. The apparatus of claim 1, further comprising at least one return electrode capable of being disposed within the organism.

3. The apparatus of claim 1, wherein the apparatus further comprises in combination a metallic case, the metal case holding the generator and serving as the return electrode.

4. The apparatus of claim 1, wherein the first pulse and the second pulse are paired pulses.

5. The apparatus of claim 1, wherein the first pulse and second pulse are current pulses.

6. The apparatus of claim 1, wherein the first pulse and second pulse are voltage pulses.

7. The apparatus of claim 1, wherein the corresponding pulse parameter is selected from the group consisting of pulse width, pulse amplitude, pulse frequency, pulse rise time, pulse fall time, and pulse shape.

8. The method of claim 1, wherein the first pulse has a first begin time and a first end time and the second pulse has a second begin time and a second end time, and wherein the generator is configured to adjust a time delay between the first end time of the first pulse and the second begin time of the second pulse, wherein the time delay determines a size and location of the deep suprathreshold potential area.

9. A method of inducing action potentials at an adjustable locus of electrically excitable tissue within an organism with a generator, the method comprising the steps of:
    delivering a first pulse of electrical stimulation to the tissue using a first set of at least one cathode within an array of electrodes implanted near the tissue to generate a first action potential area and a first subthreshold potential area in the tissue with respect to a return electrode disposed within the organism;
    delivering a second pulse of electrical stimulation to the tissue using a second set of at least one cathode within the array to generate a second action potential area and a second subthreshold potential area in the tissue with respect to the return electrode; the second pulse substantially non-simultaneous with the first pulse;
    adjusting a first pulse parameter of the first pulse to cause a corresponding adjustment of the first subthreshold potential area; and adjusting a second pulse parameter of a second pulse to cause a corresponding adjustment of the second subthreshold potential area; and wherein a deep tissue suprathreshold potential area results from a superposition of the first substhreshold potential area and second subthreshold potential area.

10. The method of claim 9, wherein the step of adjusting the first pulse parameter includes the step of increasing a pulse width to cause an increase of the corresponding first subthreshold potential area.

11. The method of claim 9, wherein the step of adjusting the second pulse parameter includes the step of increasing a pulse width to cause an increase of the corresponding second subthreshold potential area.

12. The method of claim 9, wherein the step of adjusting the first pulse parameter includes the step of decreasing a pulse width to cause a decrease of the corresponding first subthreshold potential area.

13. The method of claim 9, wherein the step of adjusting the second pulse parameter includes the step of decreasing a pulse width to cause a decrease of the corresponding second subthreshold potential area.

14. The method of claim 9, wherein the first pulse has a first begin time and a first end time and the second pulse has a second begin time and a second end time, and wherein the generator is configured to adjust a time delay between the first end time of the first pulse and the second begin time of the second pulse, wherein the time delay determines a size and location of the deep suprathreshold potential area.

15. The method of claim 9, wherein the first pulse has a first weighted average time and the second pulse has a second weighted average time, wherein the generator is configured to adjust a time delay between the first and second weighted average times, wherein the time delay determines a size and location of the deep suprathreshold potential area.

16. The method of claim 9, wherein the first pulse has a first peak time and the second pulse has a second peak time, wherein the generator is configured to adjust a time delay between the first and second peak times, wherein the time delay determines a size and location of a suprathreshold potential area.

17. A method of inducing an action potential at an adjustable locus of electrically excitable tissue within an organism using a two-dimensional array of electrodes comprising the steps of:
implanting the two-dimensional array of electrodes near the tissue;
selecting at least two electrodes from the two-dimensional array of electrodes;
for each of the at least two selected electrodes, delivering a substantially non-simultaneous corresponding pulse of electrical stimulation to the tissue to generate an action potential area and a subthreshold potential area in the tissue with respect to a return electrode disposed within the organism, the corresponding pulse having a corresponding pulse parameter;
adjusting the corresponding pulse parameter for at least one of the selected electrodes to cause an adjustment of the corresponding subthreshold potential area, and wherein a deep tissue suprathreshold potential area is induced from a superposition of the two subthreshold potential areas.

18. The method of claim 17, wherein the step of adjusting the corresponding pulse parameter includes the step of increasing a pulse width to cause an increase of the corresponding subthreshold potential areas.

19. The method of claim 17, wherein the step of adjusting the corresponding pulse parameter includes the step of decreasing a pulse width to cause a decrease of the corresponding subthreshold potential areas.

20. The method of claim 17, wherein the step of adjusting the corresponding pulse parameter includes the step of adjusting a pulse parameter selected from the group consisting of pulse amplitude, pulse width, pulse rise time, pulse fall time, and pulse shape.

21. A method of inducing action potentials at an adjustable locus of electrically excitable tissue within an organism with a generator, the method comprising the steps of:
delivering a first pulse of electrical stimulation to the tissue using a first set of at least one cathode within an array of electrodes implanted near the tissue to generate a first action potential area and a first subthreshold potential area in the tissue with respect to a return electrode disposed within the organism;
delivering a second pulse of electrical stimulation to the tissue using a second set of at least one cathode within the array to generate a second subthreshold potential area in the tissue with respect to the return electrode; the second pulse substantially non-simultaneous with the first pulse;
adjusting a first pulse parameter of the first pulse to cause a corresponding adjustment of the first subthreshold potential area; and
adjusting a second pulse parameter of a second pulse to cause a corresponding adjustment of the second subthreshold potential area; and
wherein a deep tissue suprathreshold potential area results from a superposition of the first substhreshold potential area and second subthreshold potential area.

22. The method of claim 21, wherein the first pulse has a first begin time and a first end time and the second pulse has a second begin time and a second end time, and wherein the generator is configured to adjust a time delay between the first end time of the first pulse and the second begin time of the second pulse, wherein the time delay determines a size and location of the deep suprathreshold potential area.

23. The method of claim 21, wherein the first pulse has a first weighted average time and the second pulse has a second weighted average time, wherein the generator is configured to adjust a time delay between the first and second weighted average times, wherein the time delay determines a size and location of the deep suprathreshold potential area.

24. The method of claim 21, wherein the first pulse has a first peak time and the second pulse has a second peak time, wherein the generator is configured to adjust a time delay between the first and second peak times, wherein the time delay determines a size and location of a suprathreshold potential area.

* * * * *